(12) United States Patent
Rawat et al.

(10) Patent No.: US 8,963,914 B2
(45) Date of Patent: Feb. 24, 2015

(54) COMPUTER BASED SYSTEM AND METHOD FOR MEDICAL SYMPTOMS ANALYSIS, VISUALIZATION AND SOCIAL NETWORK

(76) Inventors: Rishi Rawat, Sunnyvale, CA (US);
Radhika Rawat, Sunnyvale, CA (US);
Rachna Rawat, Boulder, CO (US);
Rajeev Rawat, Sunnyvale, CA (US)

( * ) Notice: Subject to any disclaimer, the term of this patent is extended or adjusted under 35 U.S.C. 154(b) by 363 days.

(21) Appl. No.: 13/352,331

(22) Filed: Jan. 17, 2012

(65) Prior Publication Data
US 2012/0182291 A1 Jul. 19, 2012

Related U.S. Application Data

(60) Provisional application No. 61/433,947, filed on Jan. 18, 2011.

(51) Int. Cl.
*G06T 15/00* (2011.01)
*G06T 17/00* (2006.01)
*G06F 19/00* (2011.01)
*G06T 19/20* (2011.01)

(52) U.S. Cl.
CPC ............... *G06T 17/00* (2013.01); *G06F 19/32* (2013.01); *G06T 19/20* (2013.01); *G06T 2210/41* (2013.01); *G06T 2219/2024* (2013.01); *G06T 2219/2012* (2013.01)
USPC ............ 345/419; 345/420; 345/474; 715/771

(58) Field of Classification Search
CPC ......... G06F 19/32; G06T 17/00; G06T 19/20; G06T 2219/2012; G06T 2219/2024; G06T 2210/41
USPC ............................ 345/419, 420, 474; 715/771
See application file for complete search history.

(56) References Cited

U.S. PATENT DOCUMENTS

| | | | |
|---|---|---|---|
| 5,984,368 A | 11/1999 | Cain | |
| 6,132,218 A | 10/2000 | Benja-Athon | |
| 6,308,102 B1 * | 10/2001 | Sieracki et al. | 607/59 |
| 6,383,135 B1 * | 5/2002 | Chikovani et al. | 600/300 |
| 6,687,685 B1 | 2/2004 | Sadeghi | |
| 6,747,672 B1 | 6/2004 | Haakonsen | |
| 6,864,912 B1 | 3/2005 | Mahaffey | |
| 7,374,536 B1 | 5/2008 | Taylor et al. | |

(Continued)

OTHER PUBLICATIONS

Ghinea, Gheorghita. "3-D Pain Drawings—Mobile Data Collection Using a PDA." IEEE Explore 10.1 (2008).

(Continued)

*Primary Examiner* — Phu K Nguyen

(57) ABSTRACT

A computer system and related method for analysis of medical symptoms on a body of a living being is provided. The system comprises a first portion of computer readable medium which stores digital representation of a plurality of tissue layers in the body. The system also includes a processor unit and a second portion of computer readable medium. The second portion of the computer readable medium stores instructions executable by the processor unit to perform the steps of displaying at least one tissue layer from the plurality of the tissue layers on a display device, receiving a first input indicating a locale on the displayed at least one tissue layer, receiving a second input associating a medical symptom description to the indicated locale, and including information about the medical symptom description and the associated locale in the digital representation of the body. Related methods are also provided.

20 Claims, 16 Drawing Sheets

(56) References Cited

U.S. PATENT DOCUMENTS

| | | | | |
|---|---|---|---|---|
| 7,499,048 | B2* | 3/2009 | Sieracki et al. | 345/419 |
| 8,021,298 | B2 | 9/2011 | Baird et al. | |
| 8,139,068 | B2* | 3/2012 | Isner et al. | 345/474 |
| 8,276,091 | B2* | 9/2012 | Altkorn et al. | 715/771 |
| 2001/0041992 | A1 | 11/2001 | Lewis | |
| 2003/0139652 | A1 | 7/2003 | Kang et al. | |
| 2003/0146942 | A1* | 8/2003 | Helgason et al. | 345/968 |
| 2009/0037470 | A1 | 2/2009 | Schmidt | |
| 2009/0083231 | A1 | 3/2009 | Eberholst | |
| 2010/0070306 | A1 | 3/2010 | Dvorak | |
| 2012/0116804 | A1 | 5/2012 | Mesika | |
| 2013/0018275 | A1 | 1/2013 | Dodson et al. | |

OTHER PUBLICATIONS

Serif, Tacha, and Gheorghita Ghinea. "Recording of Time-Varying Back-Pain Data: A Wireless Solution." IEEE Transactions on Info. Tech. in Biomedicine 9.3 (2005): 447-58.

"WebMD Symptom Checker." Symptom Checker from WebMD. Check Your Medical Symptoms. N.p., n.d. Web. Jan. 27, 2010. <http://symptoms.webmd.com/>.

Ransford et. al.. "The pain drawing as an aid to psychologic evaluation of patients with low-back pain," Spine, vol. 1, No. 2, pp. 127-134, 1976.

Ghinea et al., 3-D Pain Drawings—Mobile Collection Using a PDA. Informational Technology in Biomedicine, IEEE transactions on. 2008;12.

Kellgren JH. On the distribution of pain arising from deep somatic structures with charts of segmental pain areas. Clin Sci.1939;4:35-46.

Feinstein et al.. Experiments on pain referred from deep somatic tissues. J Bone Joint Surg Am.1954;36-A:981-997.

McCall et al.. Induced pain referral from posterior lumbar elements in normal subjects. Spine. 1979;4: 441-446.

Gerber et al.. The pattern of pain produced by irritation of the acromioclavicular joint and the subacromial space. J Shoulder Elbow.

* cited by examiner

COMPUTER BASED SYSTEM AND METHOD FOR MEDICAL SYMPTOMS ANALYSIS, VISUALIZATION AND SOCIAL NETWORK

CROSS-REFERENCES TO RELATED APPLICATIONS

The present invention claims priority to the U.S. Provisional Application No. 61/433,947, titled "GATHERING, VISUALIZING AND ANALYZING PATIENT AND DOCTOR INPUT ON A 3D AVATAR TO IMPROVE QUALITY OF MEDICAL CARE, EMPOWER PATIENTS, AND FORGE NEW SOCIAL BONDS," filed Jan. 18, 2011, which is herein incorporated by reference.

BACKGROUND

The present invention is generally related to techniques for analysis of medical conditions. More particularly, it provides a computer based system and method for recording medical symptoms and facilitates analysis of the recorded information to provide variety of facilities.

As the field medicine grows more complex, the task of gathering relevant patient-symptom data faces several challenges. The amount and dimensionality of medical data generated by hospitals continues to grow. Advances in computing technologies can now facilitate the collection and storage of large quantities of medical data, which can be advantageously used for treatments that are tailored to individuals.

As dimensionality grows, the granularity of medicine may increase. It may be possible to describe medical conditions more precisely and to also formulate more precise treatment plans. If properly used, high directionality may improve healthcare by reducing the chances of mis-diagnosis. On the other hand, it may be disastrous, if health workers, such as doctors and nurses, assign a treatment based on irrelevant artifacts of the data. Part of the challenge health-workers face is finding appropriate ways to infer important medical variables such as a living being's medical state, an explanation for the state (i.e. what actions led to that state), and a course of treatment.

However, in some senses, patients also face tremendous challenges in today's medical landscape, one challenge being communicating information in a format that can be understood and used by a health-worker. This may be difficult because the information may describe something that is difficult for the worker to observe (such a living being's perceived symptoms feelings of symptoms). It may additionally be difficult because precise, accurate communication may involve the patient understanding complex medical terminology, such as terminology describing anatomy, or medical conditions, or medical treatment procedures.

Another challenge that also plagues the medical field can be summarized by the notion that people are "only human." That is, human errors on the part of at patient or a health worker may lead to undesirable outcomes. One difficulty a patient might have is memory; they may, for example, forget the details of past symptoms, or may mis-remember them. A corresponding error on the side of a health worker could be misplacing a portion of person's medical file, or brushing over important details while scanner a patient's file. Such errors may certainly carry the potential to do lasting damage to a patient. A failure to consider a representative and accurate subset of a person's medical symptoms may lead the path towards misdiagnosis.

An additional challenge is that patients may often feel "alone," or isolated by the growing complexity of medicine. One may, for instance, feel powerless and weak in the company of health-workers who may seem extraordinarily knowledgeable. The patient representative may feel pressured to put faith in health-workers' ability for providing quality medical advice. However, empowered patient representatives who take an active role in the medical process may actually contribute to a higher quality diagnosis and treatment. One struggle in healthcare is thus to empower patient representatives.

A further challenge that exists for many patients is developing an understanding of their own body: their strengths, weakness and limitations from a medical perspective. As medicine becomes increasingly complex, and as medical procedures and tests become harder for the general public to understand and interpret, a patient may have difficulty assimilating information about his symptoms. Thus, over time, he may fail to recognize detrimental trends, habits, and life-style choices. This is remarkable because vigilance is a one key for preventing early onset of disease. Staying constantly watchful alert and empowered, patients who learn to observe, monitor and track patterns in their behavior have the power to learn from mistakes and improve their medical condition over time. Alas, it seems too often that medical knowledge is used to treat illness which could have been prevented, had the patient realistically understood the condition of his/her body and acted in a manner to improve it. Thus, one challenge in healthcare is educating patients about their own medical symptoms, helping them get in touch with their bodies so that they can make more responsible lifestyle choices.

To help a patient live a better life, it might not simply be enough for a health worker to deduce a medical cause and identify a treatment plan. One additional challenge is arming patients with logical and social reinforcement that may assist him/her in living a healthier life.

Accordingly, the present invention provides computer-based techniques for improved medical symptoms analysis that can address one or more challenges described above and others.

SUMMARY OF THE INVENTION

It is an object of the present invention to provide computer-based techniques for analysis of medical conditions. More specifically, the present invention provides a computer based system and method for analysis, visualization and social networking for medical conditions.

In a specific embodiment, the present invention provides a computer system for analysis of medical symptoms on a body of a living being. The system comprises a first portion of computer readable medium, which stores a digital representation of the body. The digital representation of the body comprises representation of a plurality of tissue layers at a plurality of depths in the body, respectively. Each of the plurality of the tissue layers can be a three dimensional representation. The system also comprises a processor unit and a second portion of computer readable medium that stores instructions executable by the processor unit. The instructions are executable to perform the steps of displaying at least one tissue layer from the plurality of the tissue layers on a display device, receiving a first input indicating a locale on at least one displayed tissue layer, receiving a second input associating a medical symptom description to the indicated locale, and including information about the medical symptom description and the associated locale in the digital representation of the body. In alternative specific embodiments, the related methods are also provided.

Various benefits and/or advantages may be obtained from the present invention. For example, the present invention can facilitate an easy to use process using readily available computer technologies for recordation of medical symptoms over a period of time. Moreover, the present invention can facilitate variety of analyses on the recorded information. Depending upon the embodiment, the analyses can facilitate variety of applications. For example, the analysis can facilitate identification of subjects with similar medical conditions, which can further facilitate forming a social network among them. As another example, the social network can be used to assist in medical diagnosis.

The invention can facilitate providing users a better understanding of the body. Notably, this may not necessitate an in depth study of biology on users' part. The interactivity of the data collection can facilitate creating a link between the scientific practice of medicine and an intuitive grasp of health. While the technicalities of medical practice can be too detailed for users to incorporate into their daily understanding, embodiments of the present invention can permit them to incorporate visualization, symptom data, and various results of symptom analysis into their habitual conception of health. This can contribute to a greater attention on medicine as a personal, user-focused science. Embodiments of the invention can contribute to higher user awareness and connectivity to health.

Embodiments of the present invention may contribute to higher user awareness and connectivity to health, thus alleviating a degree of the isolation patients/representatives feel in the healthcare system. Thus, embodiments may include tools which may help people group together socially to accomplish a common goal of managing and improving health.

It can also aid representatives and patients alike in maintaining adequate and extensive records, identifying trends, and a host of other functions that are often either exaggerated or neglected through typical human memory of symptoms.

These and other various objects, features, advantages, and benefits of the present invention can be more fully appreciated with reference to the detailed description and accompanying drawings that follow.

BRIEF DESCRIPTION OF THE DRAWINGS

Embodiments of the present invention are illustrated in the figures of the accompanying drawings. The figures are provided to aid thorough understanding of the invention and are exemplary rather than limiting. Based on the present teachings, person of ordinary skill in the art can contemplate various alternatives, variations and modifications to the illustrated embodiments within the scope of the invention disclosed herein.

DETAILED DESCRIPTION OF THE INVENTION

The following detailed description of the invention refers at various places to the accompanying drawings and specific environments, applications, platforms, examples, computer screenshots, and implementations. The detailed description is provided for thorough understanding of the present invention and is illustrative rather than limiting.

The present invention can be generally understood as a system and method for interactively collecting, storing, and analyzing medical data from a user via computer interpretable instructions (computer program). Medical data can be understood as any data, which may correlate with the health of a living being, such as symptom data. In a specific embodiment of the present invention, interactivity may be understood to occur via a user-interface, which is the point where interaction between humans and machines occurs. It can be understood as hardware and software components that provide a means of input and output, allowing the user to manipulate a system, and allowing the system to indicate the effects of the user's manipulation, respectively.

Figure 1:
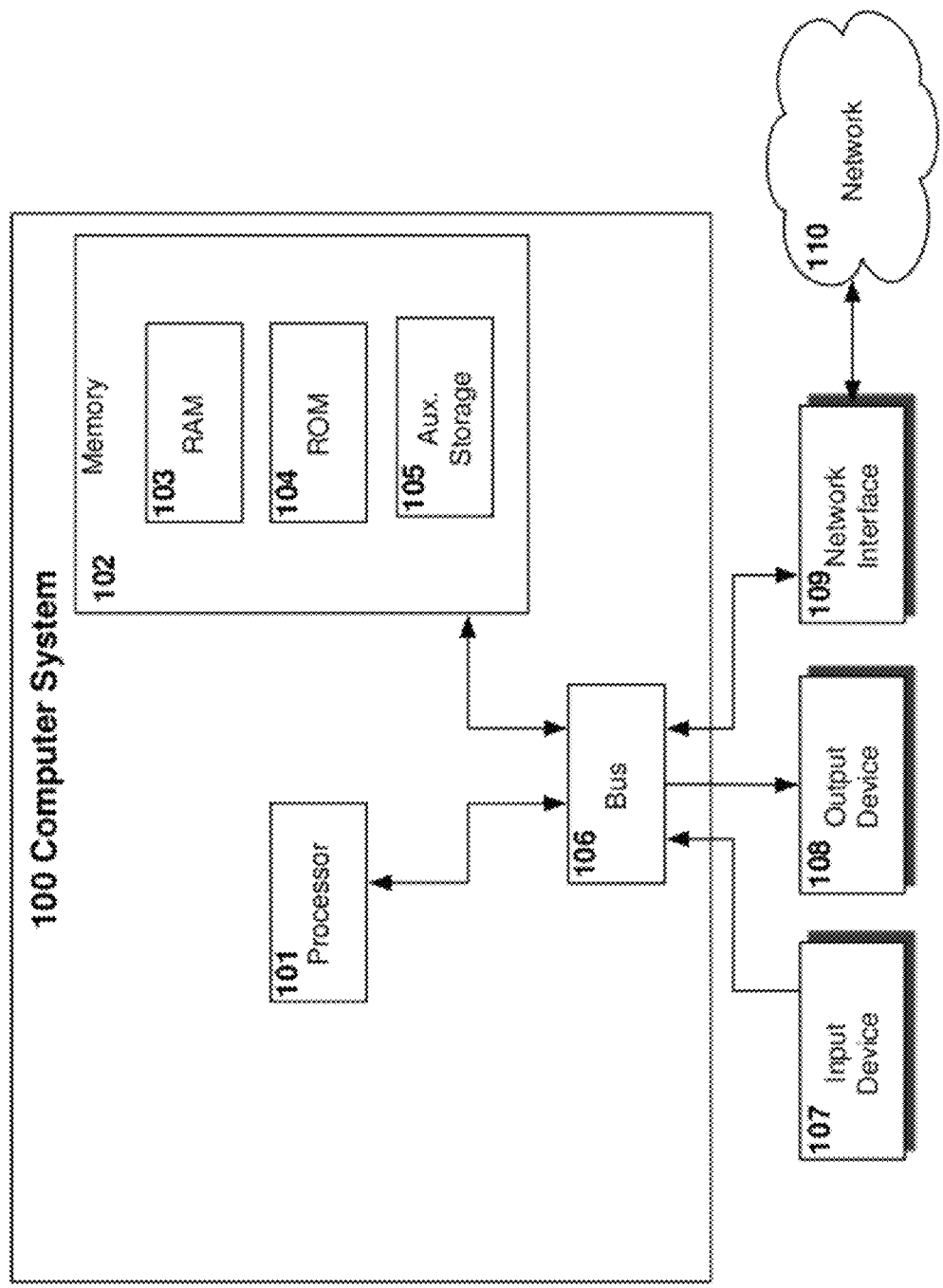
FIG. 1 illustrates an exemplary computer apparatus in a specific embodiment of the present invention.

FIG. 1 illustrates an exemplary implementation of a computer system, which the present invention can utilize in a specific embodiment. The computer system may include a processor unit 101 which may communicate with data stored in memory 101 via a system bus 106. Memory may include RAM 103, ROM 104, and Auxiliary Storage 105, such as a hard drive, or other memory components, which can be used to read and/or write information.

The processor 101 may also communicate with input devices 107 via the system bus 106. The input device(s) may include any peripherals by which a user can provide data and control signals to the computer. These signals may be single or multi modal, where modes of input are audio, video, mechanical input, etc. Examples of input devices include computer mouse, computer stylus, touch screen, keyboard, camera, video camera, microphone, motion sensors, accelerometers, natural input devices (such as the Microsoft Kinect, or the Microsoft Surface, which may allow users to carry out relatively natural motions, movements or gestures that may quickly control the computer), physical device representing a living being, where regions of the device are sensitive to touch, and additional input devices, some of which may combine multiple types of user input.

Additionally, the processor 101 may communicate with output devices 108 via the bus 106. Output devices are used to transmit signals from the processor, and may be used to signal the user.

Additionally, the processor 101 may communicate with a network interface 109 via the bus 106. The network interface may facilitate the transfer of information across an informational network 110, which will be described in more detail below.

In the specific embodiment, the user can input medical symptom data via Graphical User Interface (GUI) elements, which can be understood as graphical icons and visual indicators (shown on a display device) that a user may employ to interact with a computer system. For instance, the user can enter text describing a symptom via a GUI text-box. To associate this medical symptom with a 3D locale on a Body Layer, additional user input may be handled (in a manner discussed below). Then, the specific embodiment may create a computer-object can with data attributes to store both the symptom data and the location information can be appended to the DBR to save the information. In general, many types of symptom data can be tagged including textual, audio, visual and numeric data. In an additional embodiment, it may be possible to tag any time of symptom data that can be represented in a computer-readable format.

In the context of a specific embodiment, the interactivity may be provided via a process of a user providing an input signal to the computer via an input device 107, the processor 101 interpreting a digital representation of the signal, the processor 101 modifying a state in memory 102 via the bus 106, and the processor outputting a signal which gets communicated to the user via an output device 108.

The present invention may be understood in the general context of a series of computer executable instructions, such as program, being executed by a computer. Such computer instructions can include tasks that involve creating or modifying various types of data structures. These tasks may often be implemented on a single computer, yet they may also be performed in distributed computing environments, where a network links together remote computational devices.

Figure 2:
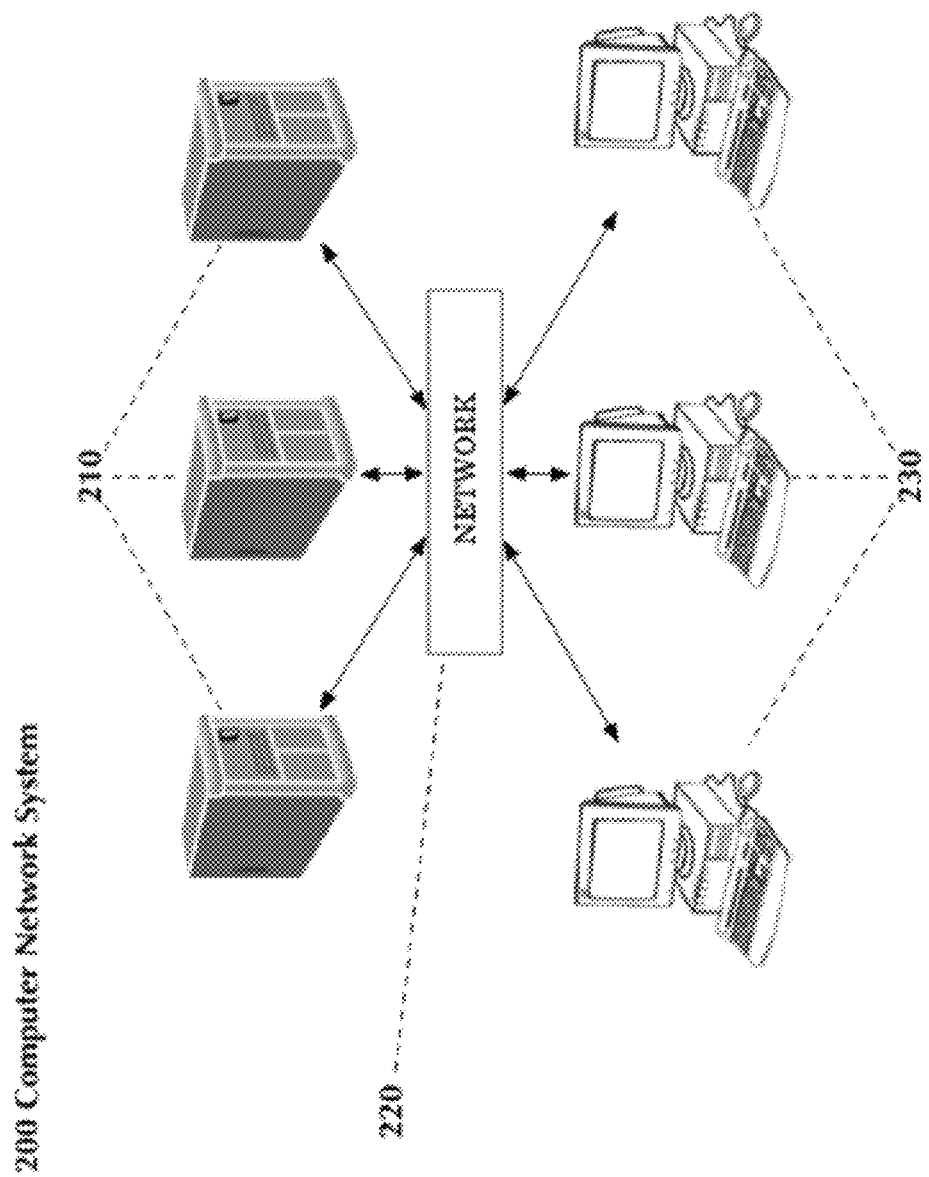
FIG. 2 illustrates an exemplary computer network system in a specific embodiment of the present invention.

FIG. 2 illustrates an exemplary computer network system 200 in a specific embodiment of the present invention. Multiple end user computers 230 and multiple server computers 210 can be coupled to a computer network 220. The computer system 100 may represent any of the end-user computers 230 or any of the servers 210. Any of the computers can be connected to the network using wired and/or wireless communication technologies. The computer network 220 can be a private network of the organization. In an alternative embodiment, the computer network 220 can include the local area network (LAN). In a further alternative embodiment, it can include the Internet. In an additional further alternative embodiment, it can include a peer-to-peer network. The end user computers can include desktops, laptops, tablets, smart phones, game-consoles, etc. The server computers can include ftp servers, application servers, mail servers, file servers, print servers, terminal servers, web server, database server, authentication server, etc. The various computers connected to the network can exchange digitized information. The exchange can occur using techniques such as Internet Protocol (IP), HTTP (Hypertext Transfer Protocol), XML (Extensible Markup Language) and others.

The present invention may be operational with numerous other computing system environments. In various embodiments, the precise location of storage and execution of the computer executable instructions may vary. For example, in one alternative, the end-user computers 230 may feature minimal processing and memory storage facilities, and the server device(s) 210 may perform the bulk of information storage and processing. In one of such embodiments, the end-user computer can be understood as kiosk, which provides a means for a user to provide input and observe output from one or more servers. In an alternative embodiment, end user devices 230 may do more processing and data storage, and examples of such devices may include smart phone, tablet or a PC end user device.

Provided below is a more detailed description of Digital Body Representation.

A specific embodiment of the present invention uses a computer-object called a Digital Body Representation (DBR) to store a living being's health/medical data in computer memory 102. The specific embodiment uses data within the DBR to assist in: gathering input from a user, displaying information to a user (via output devices), analyzing the user's medical symptoms.

Figure 3:
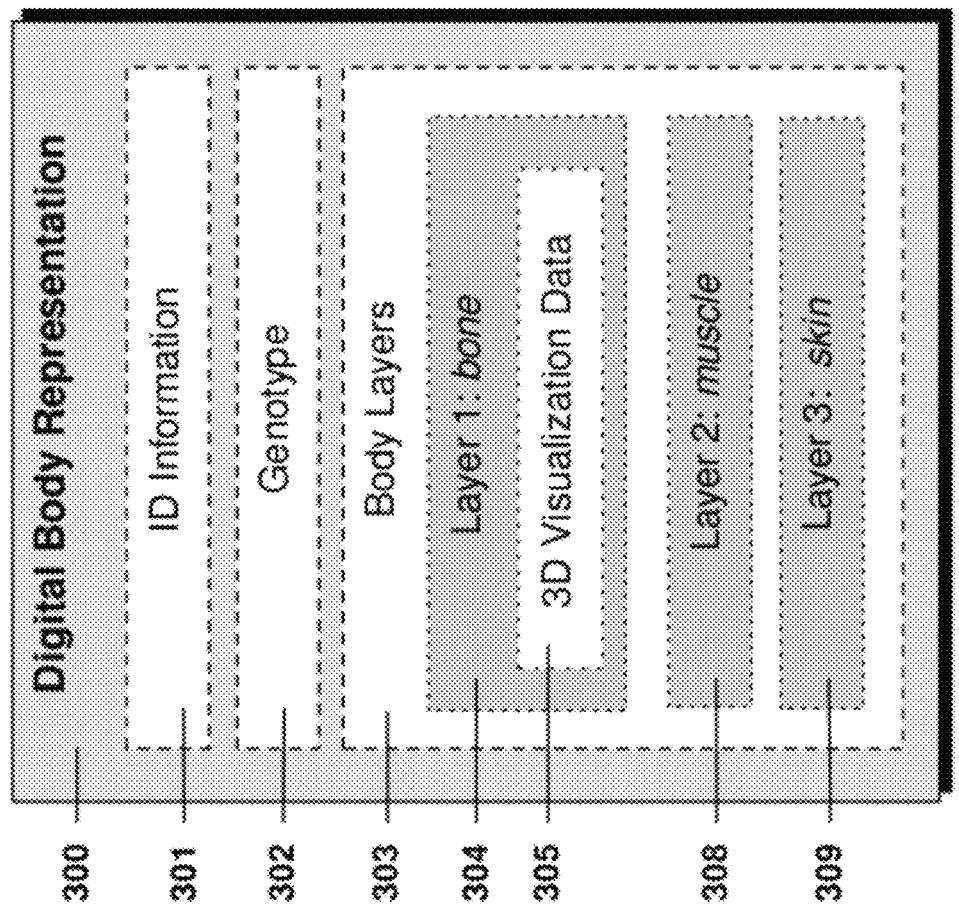
FIG. 3 illustrates an exemplary Digital Body Representation in a specific embodiment of the present invention.

FIG. 3 illustrates an exemplary DBR of a specific living being in a specific embodiment of the present invention. Various types of data relevant to the living being's health can be stored within the DBR, and some of these data may include temporal elements. For example, a DBR 300, may include data that identify a living being 301 (e.g. name, ID number, etc.), genotype sequences 302, or descriptions of his/her DNA. Additionally, the DBR can also store additional information such as physical characteristics, birth date, doctor name, family members, and other data. The DBR may contain symptom data, which describes one or multiple aspects of the living being's health at specific time(s) or over a time range. For example, a symptom data may indicate that a living being is experienced swelling on his arm on a specific day. The specific embodiment may associate temporal information describing times or durations of times with any data stored in the DBR. Thus, the DBR of the specific embodiment can be understood as a mutable object that can change over time; data operations such as appending, changing, or removing data are some possible ways to change information in this DBR 300.

In the present embodiment, medical/health data of an individual may be added to the DBR via typical user-interfaces and means of input for end-user computers 230. For example, in some configurations of a computer system, an individual may enter some medical data through a command line user interface, or via a graphical user interface (GUI) elements, such as text-boxes or menus that are shown on a display device.

Additionally, the DBR of the specific embodiment contains two or more Body Layers 303, which may be advantageous for facilitating user input. Body Layers include 3D visualization data 305 for a subset of body tissues, which can be used to display the tissues on a device to assist in the gathering, displaying and analyzing medical information. For clarity, the three dimensions, 3D, may be understood in terms of three dimensions in positional space, such as along 3 coordinate axes (e.g. [x,y,z] or [up-down, left-right, forward-backward]).

Body Layers in the specific embodiment include bone layer 304, muscle layer 308, and skin layer 309; however Body Layers are not necessarily limited to these three layers. Each Body Layer may include any subset of tissues in the body. Thus, Body Layers in a specific embodiment may include the tissues grouped by tissue type (e.g., epithelial layer, endothelial layer, innervated tissue layer etc.), function (e.g., digestion layer, respiration layer, nervous system layer etc.); however, the invention is not limiting in the types of tissues that may be grouped together to form Body Layers. Preferably, at least some portion of any two layers in the DBR can represent tissues at different depths from the surface of the body.

As an aside, before disclosing in detail methods for interacting with DBRs, the reader should note that the invention allows the DBR to be represented in computer memory 102 in various ways. For example, the specific embodiment implements a data-structure for a DBR via a nested, object oriented paradigm, where computer objects consist of data fields which may reference other objects, computer-readable data (byte code representations of numerical data, audio, video, and other data), or other information. Thus a DBR 300 of a specific living being is an instance of an object, as are the Body Layers (304, 308, 309) that it references. Objects in the specific embodiment are mutable, which means that data may be modified or appended to them.

Figure 4:
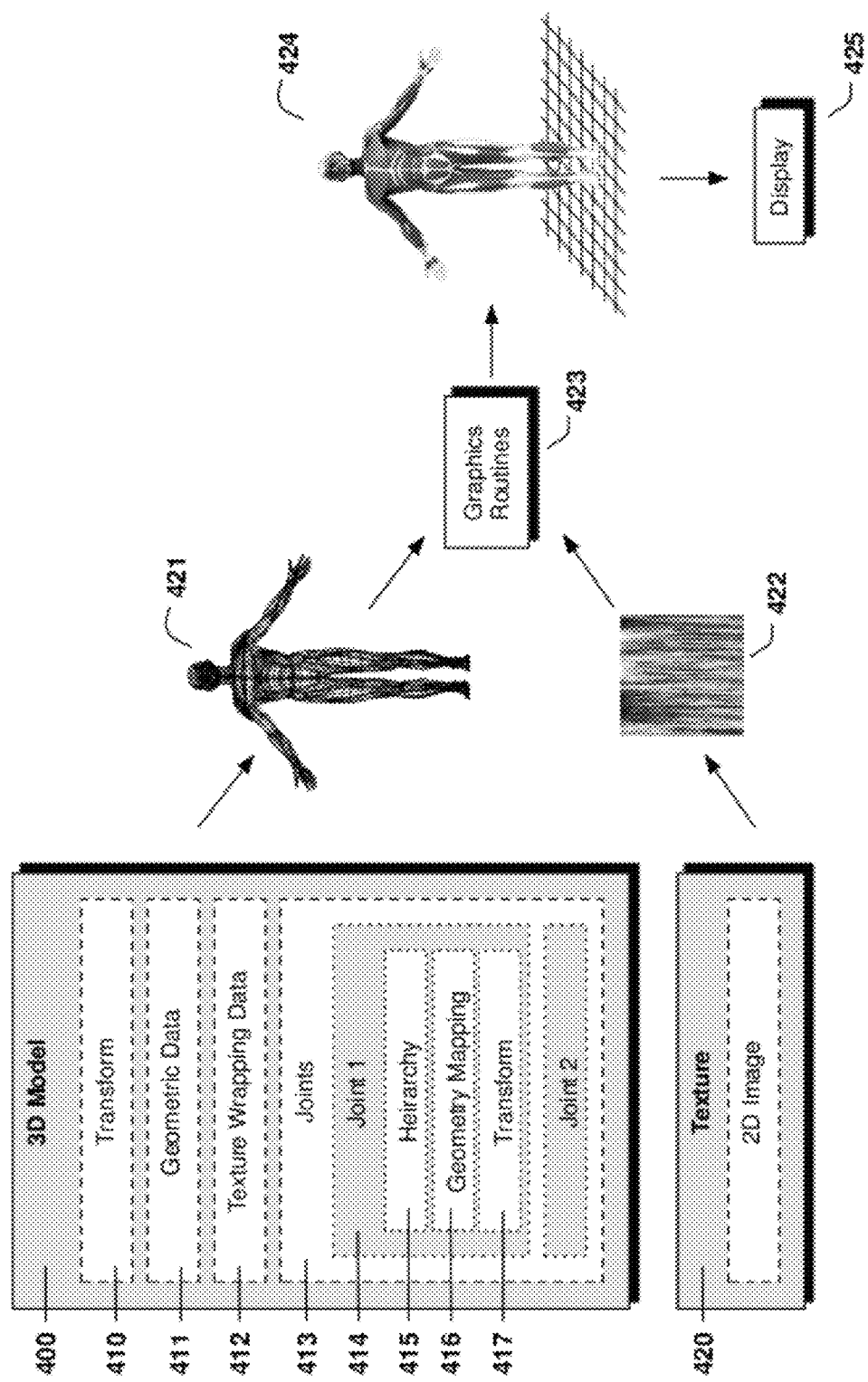
FIG. 4 illustrates 3D visualization data of a Body Tissue Layer in a specific embodiment of the present invention.

FIG. 4 illustrates the 3D visualization data of a Body Layer in a specific embodiment of the present invention. In the specific embodiment, 3D visualization data includes structural information and Texture data 420 describing the structures' shading, detail, and other information.

In the specific embodiment, the structural information is contained in a 3D model 400 including structural geometric data 411 that defines the shape of the Body Layer in 3D space. For example, in a specific embodiment, geometric data may include a collection of 3D vertices (points in 3D space), connected by various mathematical entities (such as triangles, lines, curved surfaces, etc.). Thus, geometric data may provide a mathematical representation of 3D shape, which may be illustrated as a wire-frame consisting of connected vertices 421.

In the specific embodiment, texture data 420 can be understood as information that can be applied to the 3D model in order to shade its appearance (e.g. to texture a wireframe). In one embodiment, texture data can take the form of a 2D image 421, such as a bit-map image, where patterns and colors on the image contain texturing information for the 3D model.

In the specific embodiment, computer graphics software applies the texture data 420 to the 3D model 400, creating a textured 3D Body Layer in a simulated, virtual 3D scene 424: a computer object that includes data describing the position and rotation of 3D objects. Additionally, the computer graphics software in the specific embodiment processes the data contained within the virtual 3D scene to create output signals that can be visualized by an end-user on a display device 425, a type of output device 108, which provides visual feedback to a user (such as a computer monitor/screen, television, printer, 2D/3D projector, etc.). In the specific embodiment, the 3D scene can be understood as including an active and an inactive (or hidden) portion, wherein the active portion contains 3D information, which can be processed and outputted as a signal to a display device for viewing, whereas 3D information contained in an inactive (or hidden portion) may not be processed and outputted for visual display. In the specific embodiment, 3D information may be communicated between active and inactive components of a 3D scene, thus at some times a 3D object may be displayed and at other times, hidden, based on which portion it is associated with.

In a specific embodiment, the computer graphics software uses a technique called texture-wrapping to apply Texture data 420, such as a 2D image, to a 3D model 400. Conceptually, the process of texture wrapping is similar to wrapping patterned paper around a plain generic box. The plain box is similar to a 3D model, in that it contains geometric information but may lack detail and texture, and like the texture-image, the patterned paper contains color and texture information, but is flat and 2D, lacking the geometrical information of the box.

In the specific embodiment, graphics software, such as Open GL (distributed by Khronos Group of Beaverton, Oreg.), uses a pre-defined mapping 412 from geometrical units (such as vertexes in the 3D model) to 2D coordinates on the Texture to wrap textures around the 3D model. Then, based on the mapping, the texture information (e.g. pixel data) is stretched around the surface of the 3D model.

In a specific embodiment, video game-engines contribute a subset of the functionality of computer-graphics routines 423. Video Game engines, (such as Unity 3D, provided by Unity Technologies of San Francisco, Calif.) can be understood as a collection of computer-executable routines, which provide application programming interface (API) for displaying and interacting with 3D models. In the specific embodiment, the processor 101 uses game-engine routines process information contained from the 3D virtual scene into signals that can be interpreted by display devices 425 to portray a visual representation of the 3D virtual scene 424. For example, a game engine may implement the process of rendering by projecting 3D data from the virtual scene 424 onto a 2D surface, which can be visualized by a computer screen. Alternative embodiments, such as embodiments using alternative display devices, may utilize different graphics routines to suit the particular configuration of the hardware components.

Provided below is a more detailed description of intuitive spatial input

Visualizations of 3D Body Layers can be used to provide interactive feedback for user input, in ways that may have advantages in certain scenarios. For instance, providing such input may induce a patient-user to pause and pay attention to how his/her body feels. It may encourage introspection, and lead to the making of a personal appraisal of the medical causes, which may be a way to empower patients. Additionally, such techniques may provide an avenue for an individual to describe medical symptoms which may be otherwise difficult to express. Furthermore, the methods outlined below may store symptom data in a regular way, with a format that may be conducive to later analysis.

Many symptoms that a person may experience have a spatial-component, which may be difficult to describe, or remember precisely. For example, some medical symptoms, such as swelling, rashes, lacerations, itching, numbness, occur over specific regions of the body at specific depths in different tissues. Additionally, symptoms may occur through a range of motion, such as when a user does an action. For example, one specific person may experience tenderness in the tendons around the knee when he raises a leg, as in going up stairs, but not while walking on a flat surface. Symptom data associated with actions is more specific, and may provide the detail required for a good medical diagnosis. Visual input via 3D Body Layers may allow users to enter data about location and movement in predefined sequence of steps, resulting in data which can be advantageous: realistic, regularized, and useful for a human trying to get in touch with his body.

Figure 5:
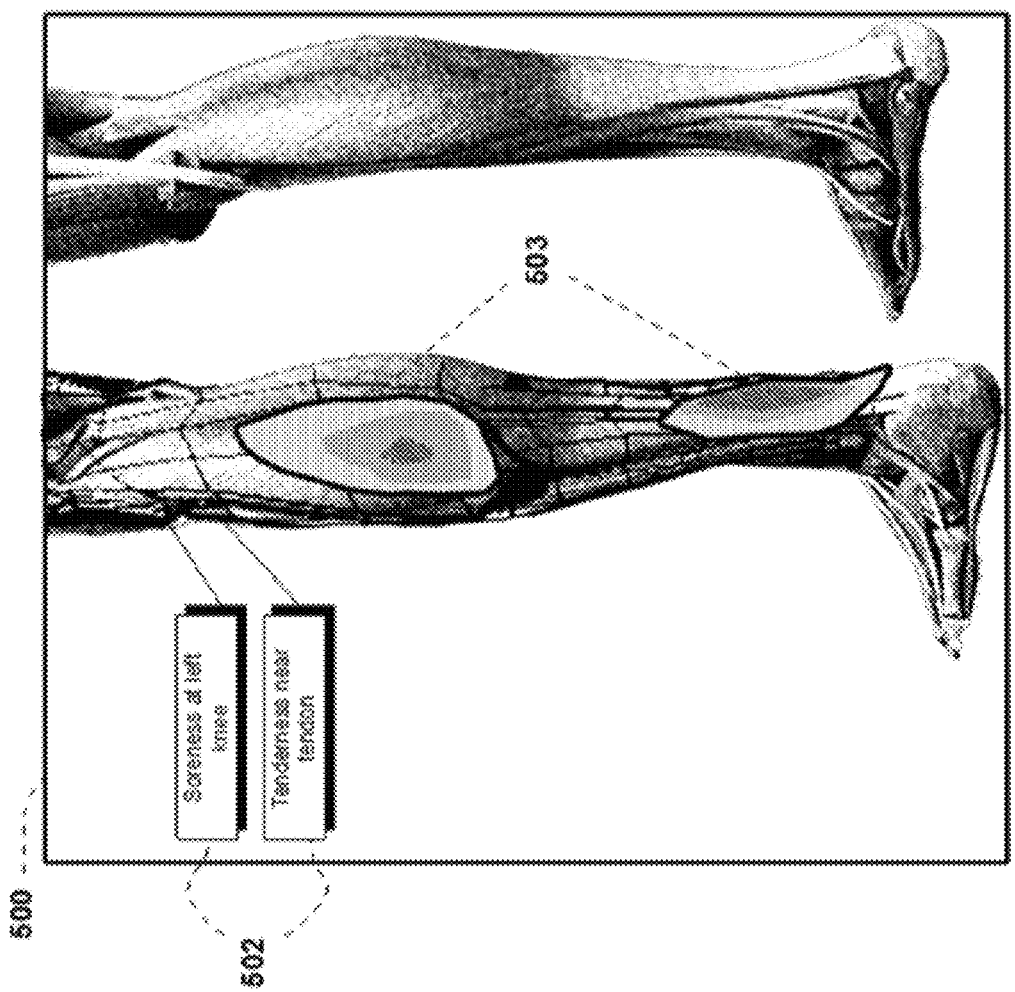
FIG. 5 illustrates an exemplary screenshot of computer monitor for a Body Layer and symptom data associated with locales on a Body Layer in a specific embodiment of the present invention.

FIG. 5 illustrates an exemplary screenshot of computer monitor for a Body Layer and symptom data associated with locales on a Body Layer in a specific embodiment of the present invention. The screenshot 500 shows a rendering of a portion of a muscle layer, a portion of a bone layer, and a portion of tendon layer, where the portion corresponds to the calve region of a person's leg. The screenshot additionally displays some user-inputted symptom data 502, 503 that are visually associated with specific locales of the muscle layer; representations of the symptoms are attached to corresponding locales on the Body Layer in the visual representation 500 presented to the end-user. For example, in the specific embodiment, some symptom data 502 can be represented by GUI elements that are connected by a line (or similar designator) to a locale.

Additionally, in the specific embodiment, symptom data 503 may be represented visually and symbolically on or near the surface of the Body Layer. These symptom data 503 may give the layer a "painted appearance," where portions of the layer may be colored/textured to represent medical information symbolically. For example, a painted region on the body of one color/texture (e.g. blue) on the layer may represent the prevalence of a first symptom (such as itch) over that region; however, a painted region with different color/texture (e.g. red) may represent a different symptom (such as swelling).

In a specific embodiment, the process for associating symptom data with specific locales on the 3D Body Layers is called tagging and may involve a user selecting one or more Body Layers, indicating a locale, indicating a symptom description, and appending tagged-symptom data to the DBR.

In a specific embodiment of the present invention, user input may be interpreted to change which Body Layers 303 are displayed and visible to the user. Recall that the virtual 3D scene defines which 3D objects may be shown in a display device. In the specific embodiment, Body Layers can be shown or hidden by changing the information that is contained within the 3D scene. That is, removing the 3D model representing the Body Layer's structure from the scene can hide a Body Layer that is visible on the display. Conversely, a Body Layer that was previously hidden can be brought back into display by adding its 3D model to the virtual scene. In the specific embodiment, user input entered via a Graphical User Interface (GUI) element, such as a menu, can change which layers are displayed. The menu allows a user to communicate information about which Body Layers to display and which Body Layers to hide to the processor 101. Then, the processor can alter objects in memory, such as the virtual 3D scene, in a manner that complies with the user's intent.

In an alternative embodiment, the user may partially-hide one or more Body Layers by changing the opacity with which they are displayed. For example, a user may set the opacity of a skin and muscle layer to a low degree (for translucence) in order to see an underlying bone-layer.

Figure 6:
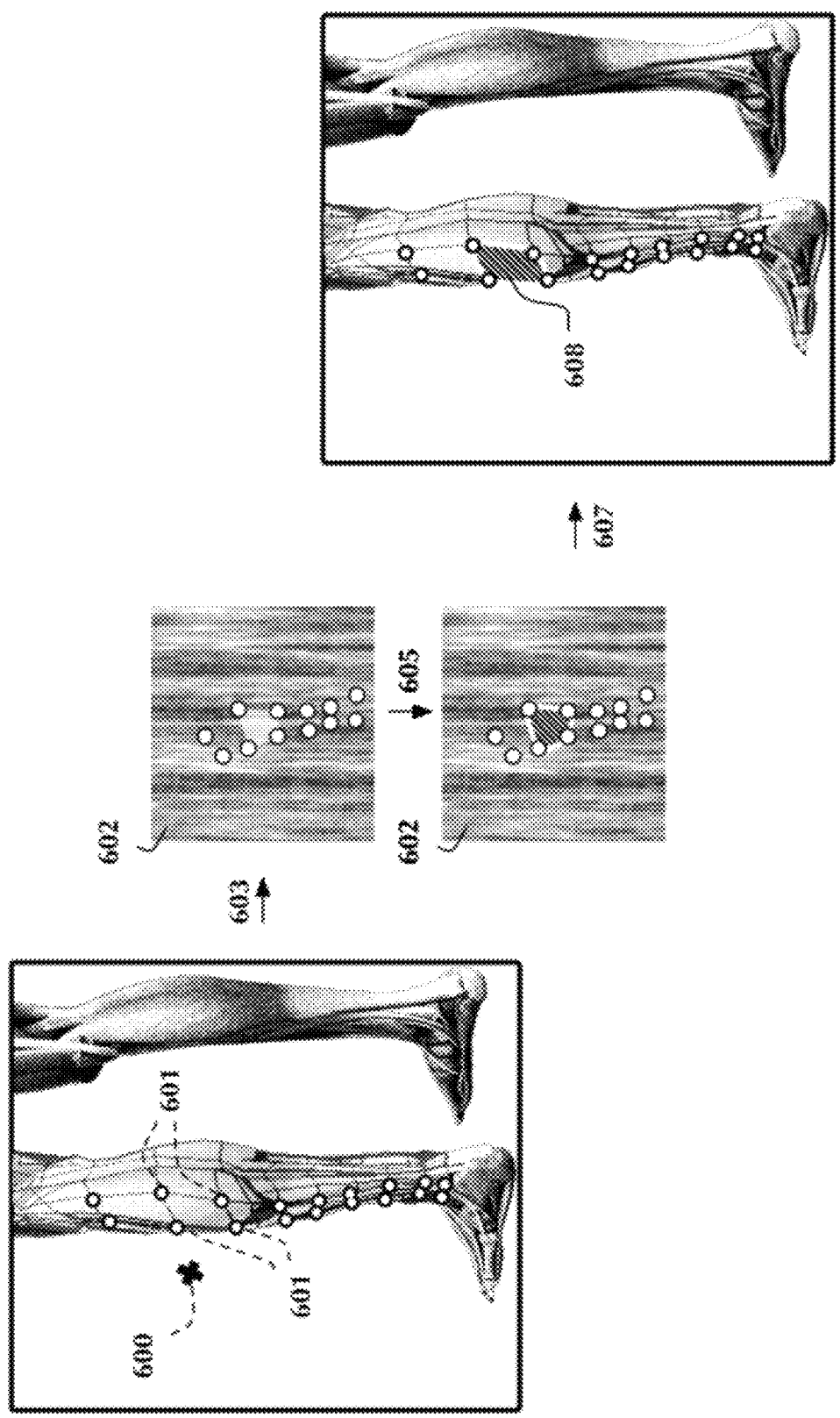
FIG. 6 illustrates an exemplary flow of steps in a method for tagging a symptom to a locale on a Body Layer in a specific embodiment of the present invention

FIG. 6 illustrates an exemplary flow of steps in a method for tagging a symptom to a locale on a Body Layer in a specific embodiment of the present invention; where tagging can be understood as associating a medical symptom with a locale on the Body Layer a DBR. In the specific embodiment, symptom data and locale information are associated via a data-object. In the specific embodiment, tagging may involve the creation of such a data-object, which may be appended to the DBR.

In the specific embodiment, flow of steps begins with the selection of one or more Body Layers to be displayed, and the specification of a symptom format. The user may, for example, use GUI elements to indicate which layer(s) should be tagged as well as whether the symptom is a textual description, or a painted symbolic description, an audio file etc. In a specific embodiment of the present invention, location tagged audio data may be converted into textual data using voice-recognition software routines.

In the specific embodiment, upon selecting layers (such as from a GUI element such as a menu), the non-selected layers are hidden, and the selected layers are displayed on the display device.

In the specific embodiment, upon the user indicating one or more layers and a symptom description (such as a textual description, audio description, visual description, or a symbolic visual pattern representing a symptom), the user may indicate a "query" locale 600 in the virtual 3D space (via methods described below). The query locale is a 3D location close to a portion of a displayed Body Layer. The query locale is used to search the 3D models of the displayed layers to find the geometrical units 601 (such as vertexes) close to the query locale. Then, a data-storage object (such as a texture-file) may be created or modified to associate these geometrical units (locale data) with symptom data. In alternative embodiments, the data-storage object may have various types and constructions, but may share a common ability to associate locale data with symptom data in memory 102. An example of other such objects include entries in a relational database.

In the specific embodiment, the query locale may be used to modify texture objects to create interactive visual symptom tagging of symbolic data (painting). As previously described, painting a symptom may cause the color of the layer at a particular locale on to change in order to reflect a system symbolically. In the present embodiment, this occurs via determining and modifying the region of the texture-image that is responsible for the texturing the layer near the query locale. As illustrated in the specific embodiment of FIG. 6, a portion of the muscle layer corresponding to the calves, has been shaded with a texture, 602, which is wrapped onto the model using a pre-defined mapping 412, in the specific embodiment. The first step requires the user to indicate (such as via a GUI, or other user interface) the symptom that he/she desires to indicate (such as swelling, itching, burning, etc.). Next, the user indicates a query locale 600, which is converted into a locale on the 3D Body Layer (by methods described below), which becomes the location where the painting will occur. Then, texture coordinates that map to the locale can be found 603 (by using the query locale to query the geometric data of the model to find close-by vertices 601, and subsequently looking up the texture coordinates for those vertices). Next, the texture can be modified (605) at these coordinates so that the body shows 608 the painted symptom when the display is updated 607. Then, the symptom data can be appended to the DBR. In the specific embodiment, the texture image is copied and appended to the DBR each time the user indicates a symptom by painting. This way, each time the user paints, the new symptom data, which is stored in the texture image gets appended to the DBR. In an alternative embodiment, the texture image is processed after painting and the symptom data is converted into a categorical format which can be stored in an alternative data object from a texture image. In an additional alternative embodiment, The process by which a user indicates a locale on the 3D Body Layer (such as 503) may vary based on specific hardware configurations, such as the types of input peripherals 107 that are used to gather user input.

Figure 7:
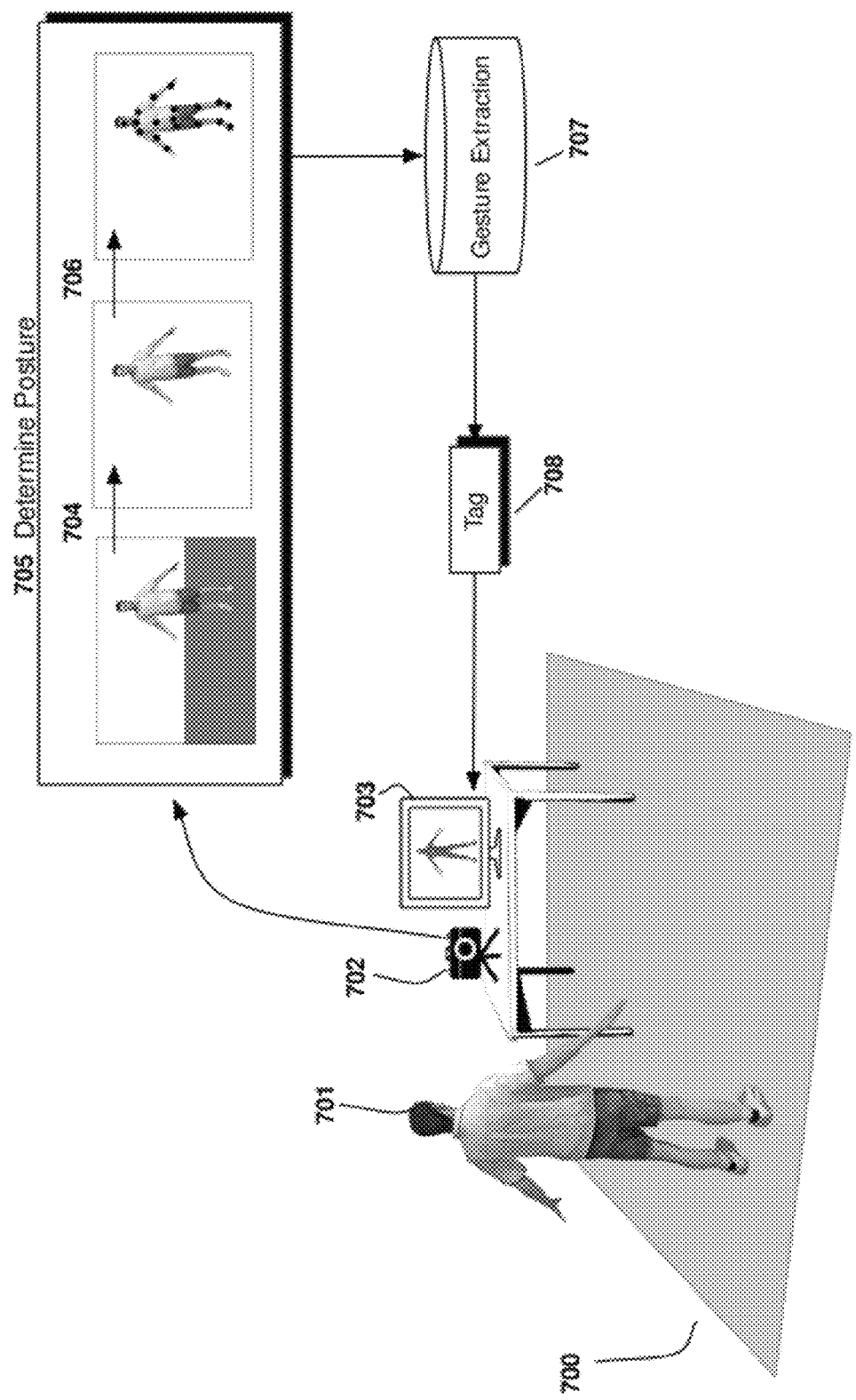
FIG. 7 illustrates an exemplary flow of steps for identifying a 3D locale using user-input from a motion sensor in a specific embodiment of the present invention.

FIG. 7 illustrates an exemplary flow of steps for identifying a 3D locale using user-input from a motion sensor in a specific embodiment of the present invention. This figure shows a space in a user's home or setting 700, which contains a motion sensor 702 (input device), and a computer monitor 703 (an output display device). The user 701 is illustrated to be standing in the range of the motion sensor where he/she can view the information displayed on the monitor.

In the specific embodiment, a user inputs information to the computer via a pre-defined set of gestures and body actions 707, which can be recorded by the motion sensor 702 and interpreted by a processor 101. Thus, via the interpretation of gestures, a user can signal the processor in various ways, to indicate for instance a type of symptom that the user seeks to input or location-tag 708.

In the specific embodiment, a user's posture is determined 705 using a pre-defined set of algorithms that process the data collected by the motion sensor. The motion sensor in the specific embodiment can be understood as a camera that takes a series of photographs over a short period of time, and uses techniques to identify parts of the images that change over time. For example, the motion sensor can use various background-subtraction schemes (704) such as background averaging to detect motion. Then, the 3D posture, or the arrangement of the user's 701 body parts in the real world 700 is inferred 706. This learning can be understood as the processor 101, forming a description in memory 102 that describes how each limb in the body is oriented in the 3D space of the real world 700. Thus, such a representation stores information that describes which parts of the body are close to each other and which parts are far.

In the specific embodiment, the process for learning the posture of the user is implemented using techniques disclosed by A. Jain, T. Thorm, H.-P. Seidel and C. Theobalt in "MovieReshape: Tracking and Reshaping of Humans in Videos," which was published in the journal, Association of Computing Machinery Transactions on Graphics (Volume 29, number 5) in 2010. However, alternative embodiments may use alternate algorithms to determine the user's position, such as specialized computer-vision algorithms, or algorithms used to infer user-position in the motion sensor called the Kinect (or Xbox Kinect) manufactured by Redmond, Wash. based Microsoft Corporation.

The specific embodiment may interpret changes in the user's posture (a gesture) as a type of input when the gesture can be recognized. In other words, the specific embodiment may respond to a gesture if the gesture can be identified among a set of pre-defined gestures 707 stored in computer-memory 102. Thus, a user may move his/her body in a particular manner to communicate a particular intent to the processor. For instance, some types of arm-movements could indicate to the processor 101 that the user wants to paint a location onto a 3D Body Layer, while another gesture may indicate to the processor that the user wants to tag a descriptive symptom to a particular part of a 3D Body Layer.

In the specific embodiment, after indicating the intent to tag some symptom data (such as for painting data similar to 503, or for tagging other data 502), the processor uses information about the user's posture and gestures to select a 3D locale on a specific Body Layer. For example, in the specific embodiment, the user can indicate a locale by "tapping" on a particular part of his body to indicate a general area of a symptom, and can subsequently indicate the Body Layer on which the user perceives the symptom by using a second gesture.

In the specific embodiment, the process of calculating the location on the 3D Body Layer corresponding to the real-life location of an area on the body that the user "tapped," involves the processor 101 analyzing the posture of the user 706 to determine which area from a pre-defined list of areas on the user's real body 701 is closest to the location of the "tap". Then, the specific embodiment uses a pre-defined mapping to find the corresponding locale on the 3D Body Layer. For example, the processor may first analyze the user's position as he taps on his body to recognize that he is tapping on the tip of his left elbow. Then, the mapping can be queried to find the 3D location of the point in the virtual 3D scene that corresponds to the tip of the left elbow for a specific Body Layer.

In an additional embodiment, user gestures may be used to specify a type of symptom to paint, such as, but not limited to swelling, itching, burning, tingling, laceration, rashes, tightness, cramps, indigestion. In a further additional embodiment, user gestures may be used to change which Body Layers are displayed (e.g. on the monitor 703).

Figure 8:
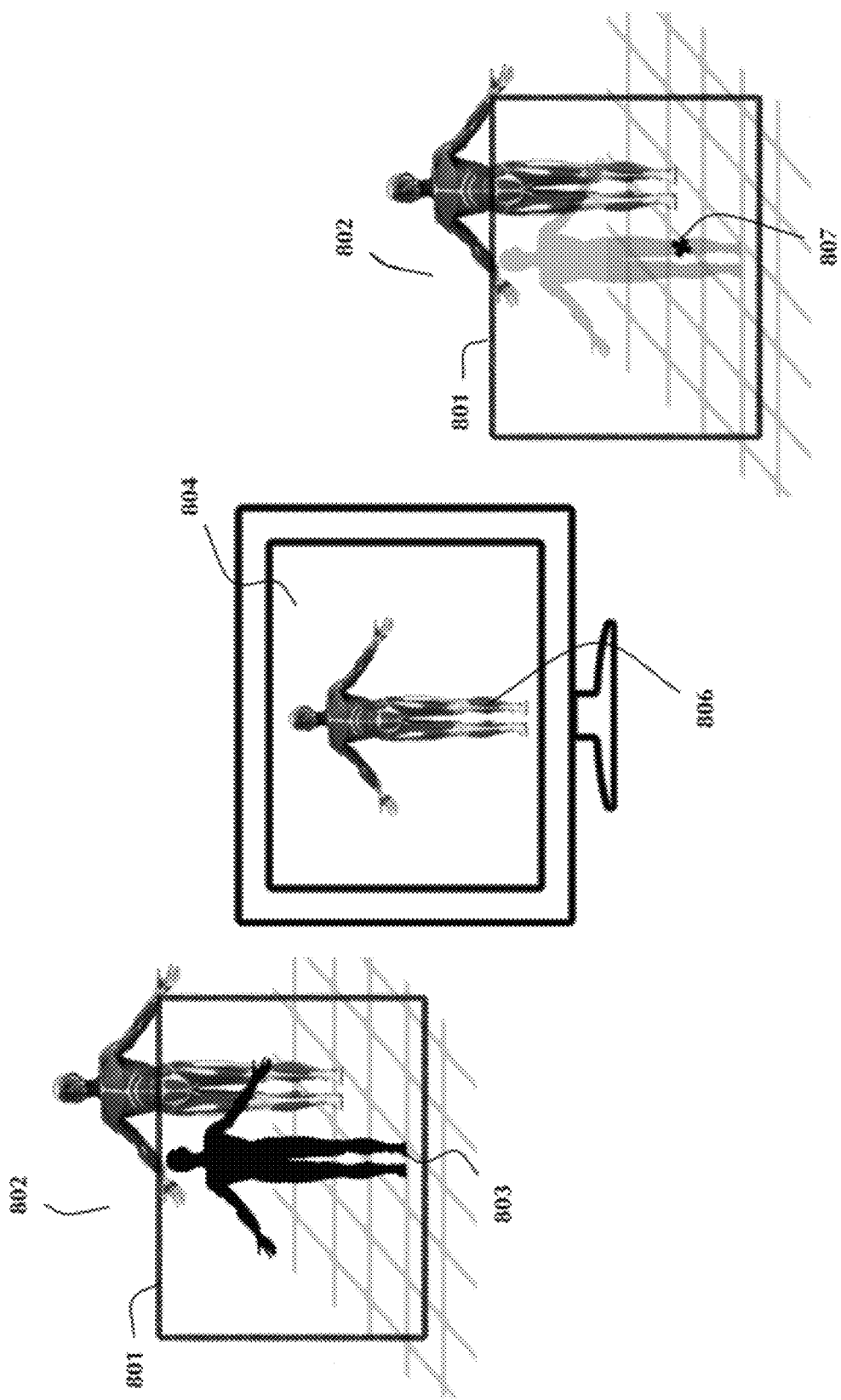
FIG. 8 illustrates an exemplary flow of steps for identifying a 3D locale based on user input using a pointing device in a specific embodiment of the present invention.

FIG. 8 illustrates an exemplary flow of steps for identifying a 3D locale based on user input using an alternative hardware setup including a computer monitor (a type of output device 108) and a pointing device (an type of input device 107) in a specific embodiment of the present invention; the specific embodiment may process or interpret user input in the form of a click on a 2D region into a 3D locale on the Body Layer that was displayed at the position of the click. For example, a user may click on a location of the leg, which is rendered on the screen of a computer monitor to indicate a specific locale in 3D.

In the specific embodiment, what the user observes on screen 804 is a rendering of a virtual 3D scene 802. For illustrative purposes, the image on the screen can conceptualized as displaying the view that might be seen from a window 801 positioned at a specific location in 3D world facing a portion of the virtual 3D scene 802. The view from the window, 801, can be described mathematically as the projection 803 of mathematical information from the 3D scene onto the window.

As a user indicates a locale by clicking (806) on a portion of the model (indicated by an X), the coordinates of the click can be mapped to a specific location 807 on the window 801 into the virtual 3D world. This specific location 807, like the window, has a definite position in the 3D virtual world. To identify a locale on the 3D Body Layer, a ray can be projected from this specific location, to find a locale on 3D Body Layer. Various algorithms may be used to determine where the ray intersects the 3D Body Layer. The specific embodiment uses algorithms packaged in a video-game engine to do this calculation.

In the specific embodiment, a user can indicate how symptoms change along a range of motion by repeatedly turning portions of the 3D Body Layer and entering symptom data for the layer in that position. In the specific embodiment, when the user location-tags a symptom, the symptom data contains an additional attribute that stores information (such the orientations and positions of the joints in the 3D model) about the 3D Body Layer's position at the time of the tagging.

This method of location tagging can be used to indicate how symptoms apply along a range of motion. For example, one specific embodiment of the present invention stores several 3D models for each Body Layer, where each 3D model describes the structure of the layer when the body is in a particular posture. Thus, one 3D model may show the musculature from a sitting position, while another 3D model may store the info of the musculature from a standing position. However, in a preferred embodiment, the user can turn/adjust/manipulate portions of a 3D Body Layer (such as moving the arm portion to change the position of the arm) to indicate various postures in a range of motion, and may append symptom data corresponding to a particular posture of the DBR. Thus a user can indicate symptoms along a range of motion by indicating symptoms along a range of postures.

Figure 9:
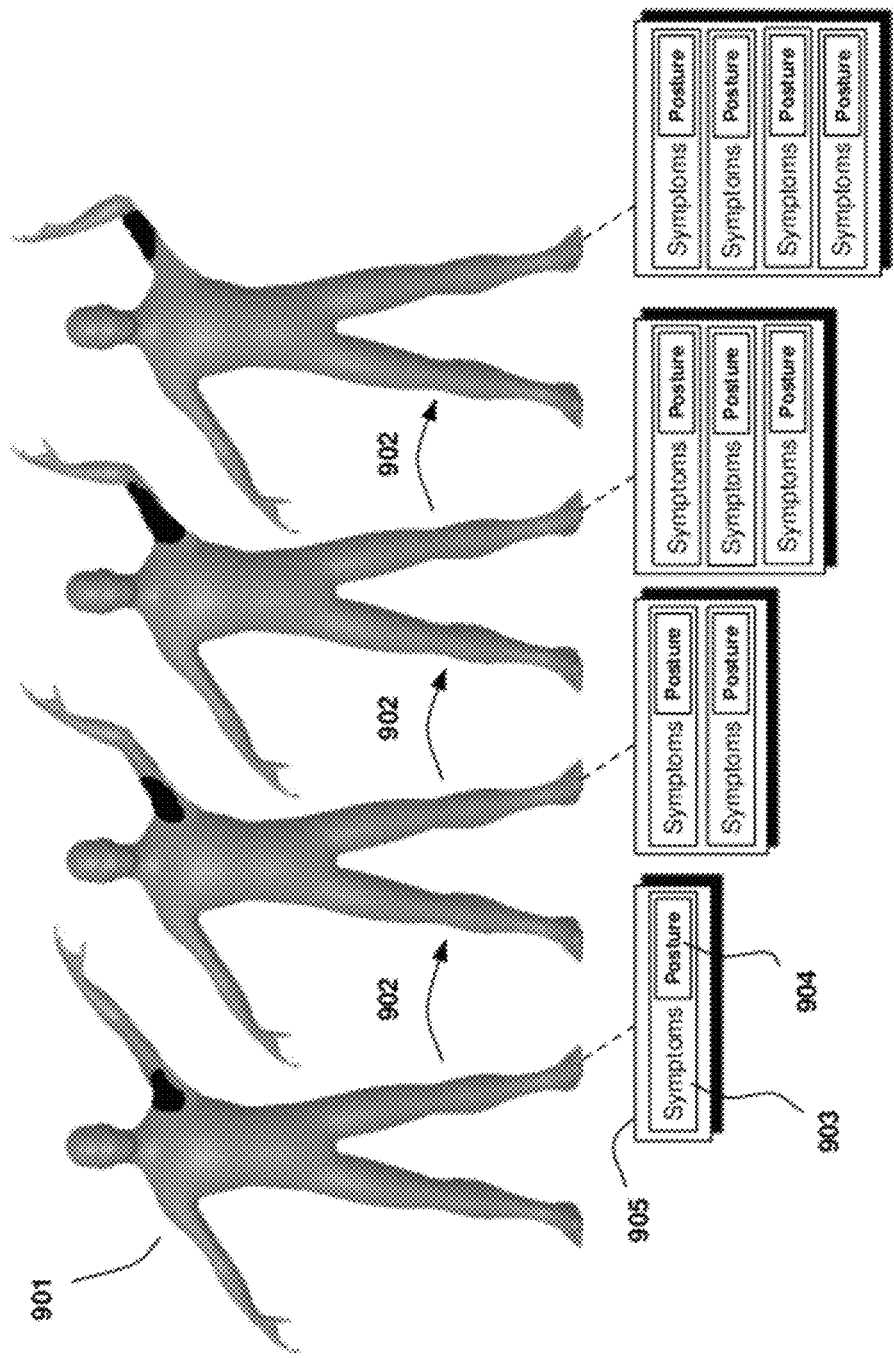
FIG. 9 illustrates an exemplary flow of steps in a method for indicating movement by repositioning a Body Layer in an embodiment of the present invention.

FIG. 9 illustrates an exemplary flow of steps in a method for indicating movement by repositioning a Body Layer in a specific embodiment of the present invention. In certain embodiments, it may be desirable to interpret patterns of user input as data indicating movement of parts of a living being. In a specific embodiment of the present invention, the user may indicate movement in a process that involves moving joints associated with a Body Layer.

The flow of FIG. 9 begins when the user has indicated (e.g., by way of GUI input) an intent to indicate motion. Then, the user repositions the displayed layer (via a process for turning portions of the body to be described below) to indicate a start position 901. From the start position, a new data object representing a portion of the movement, called a "motion description" object 905, is appended to the DBR. Motion description objects may include sequential index information, posture information 904 (values describing transforms of joints in the displayed layers), and symptom data 903.

Every time user repositions the layer, a new motion descriptor object is appended, and the symptoms tagged are associated with the corresponding motion descriptor object. Then, as long as the position is not changed, the inputted data will be associated with the motion description object. However, if the user repositions the displayed layers, a new motion description object will be created, with an incremented index (now i=1), and new data about the joint transforms. Data that are subsequently indicated are associated with this second motion description object. This process may continue with additional positions and Motion description objects until the user indicates that the movement has been indicated fully (e.g. via GUI). An object relating the motion description objects may be created to indicate that they all indicate steps along one movement. Additionally, movement description objects may contain temporal data.

The process for turning a portion of a 3D Body Layer may have additional benefits besides assisting a user in storing symptom data along a range of motion. For example, some positions of the 3D Body Layer might be hard to location tag when the 3D Body Layer is in certain positions; e.g. if the Body Layer is showing body structures of a person standing up with legs together, for it may be difficult to tag symptoms on the inside-portion of the thigh. A process to use user input to change the orientation of limbs, for example, could help to reveal locales on the body, which may need to be tagged.

Figure 10:
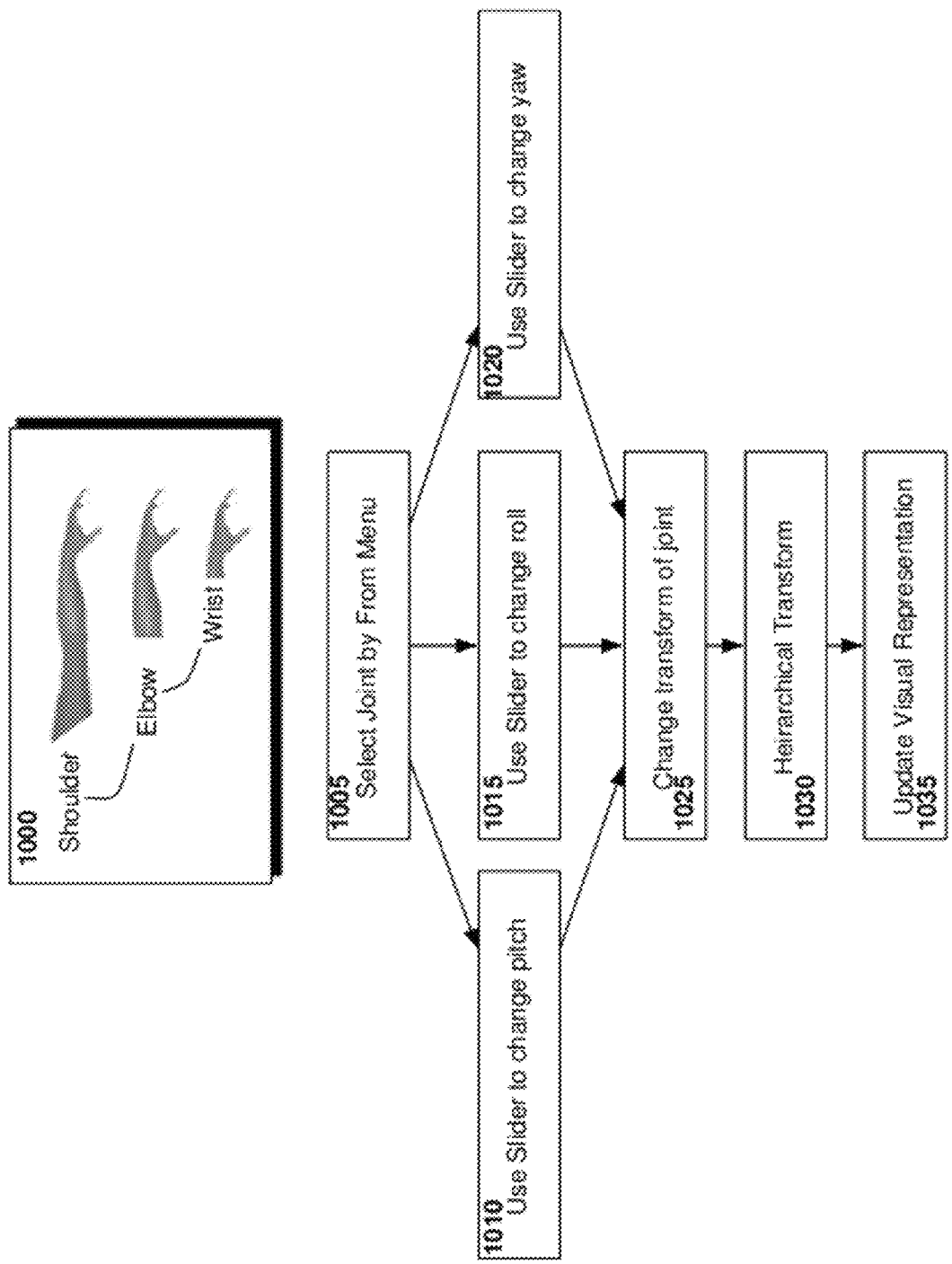
FIG. 10 illustrates an exemplary flow of steps in a method for turning a portion of one displayed Body Layer in a hierarchical manner in a specific embodiment of the present invention.

FIG. 10 illustrates an exemplary flow of steps in a method for turning a portion of one displayed 3D Body Layer in a hierarchical manner in a specific embodiment of the present invention. This may allow the user to move portions of the body in a hierarchical manner similar to how hieratically organized bones in the human body can move portions of the body. In the specific embodiment, hierarchical turning may be implemented using a set of interconnected computer-objects, which can be summarized as "joints" 413. Computer joints are associated with portions of the 3D model; they are linked to a subset of the geometric information that makes up a 3D model.

Joints are defined in a hierarchical manner 1000 understood as parent-child relationships. Thus, in the specific embodiment, a computer-joint representing the wrist is associated with all polygons from the wrist-region of the 3D model through to the finger-regions. The computer-joint for the wrist is also, as in the human anatomical model, dependent on the elbow joint, which is associated with all polygons on the 3D model from the elbow-region to the finger-region.

In this specific embodiment, the 3D representation of the layer includes individual joints (such as 414) that have defined locations in the simulated 3D space (417). The joints are ordered hierarchically (415), so modifications in the rotation/position of the parent joint modifies the rotation and position of the child-joints, e.g. spine moves elbow moves wrist. User input (such as from a GUI menu 505, which allows users to select a joint by name) can be used to turn a parent joint, causing associated geometries of child joints to be transformed. Moving a joint induces a hierarchical transform (1030).

Rotating a joint may cause these associated polygons to move. Additionally, the hierarchical relationships between joints cause child joints to move in structured ways as parent joints move; thus the polygons associated with child-joints move as well. After updating the polygon positions, the display may be updated. In an additional embodiment, hidden layers are moved simultaneously with the visible layer(s) so that for example, if a user changes which layer is displayed, the posture remains constant.

In a further additional embodiment, position data 706 from a motion sensor can be used to modify the transforms of joints in the body causing the visual representation in the display to assume the same body posture as the user.

In specific embodiments, the interactivity capabilities of the present invention may extend to using information that has been inputted into a DBR to assist a user in analyzing medical symptoms. Some types of analysis (to be disclosed below) include diagnosing of the medical condition that best explains the data in a DBR, or finding DBRs, which contain similar symptom data. However, other methods of analysis may also process and display the processing output on the visual representation of the 3D Body Layers.

In a specific embodiment of the present invention, the latter type of analysis can be understood in the context of using information in a DBR to compute a result (the result symptom), which can be displayed on the visual representation of the 3D Body Layers. Such result symptoms may be used to portray the symptom data in the DBR in a meaningful way that may help a user understand the manner in which symptoms are distributed on different locales on the body, and how a person's symptom data changes over time. An example of an analysis method that computes a result symptom and displays it on the 3D representation of a Body Layer is a method that "plays back" the symptom data in the DBR, so a user can watch the progression of symptoms through time on the Body Layer. A second analysis method that computes and displays a result symptom can be summarized as a merging-method, which takes a plurality of symptom data and displays it simultaneously on the Body Layers, so that a user may, for instance, try to observe patterns where symptoms occur.

Figure 11:
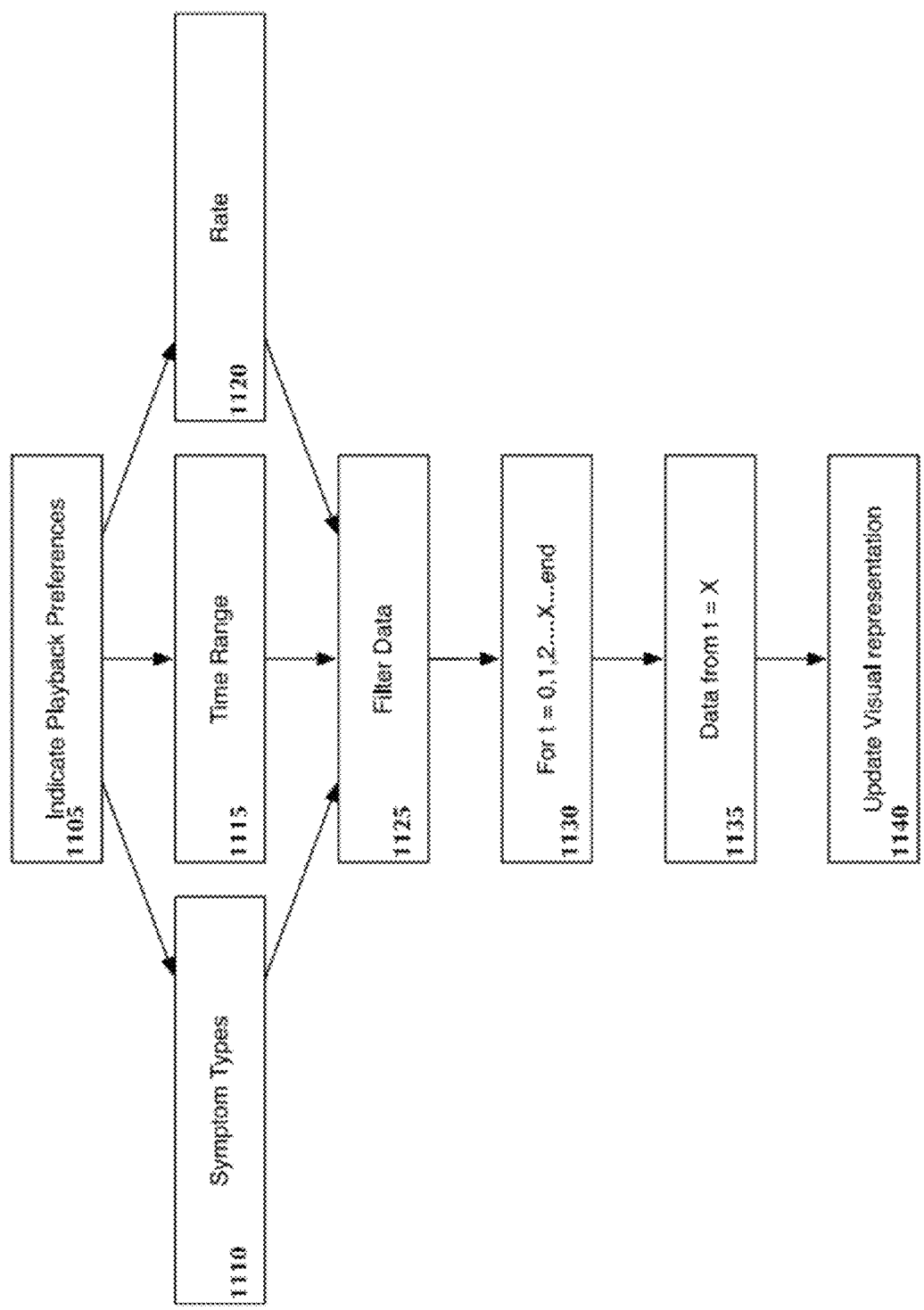
FIG. 11 illustrates an exemplary flow of steps in a method for indicating a progression of symptoms in relation to time in a specific embodiment of the present invention.

FIG. 11 illustrates an exemplary flow of steps in a method for indicating a progression of symptoms in relation to time, in a specific embodiment of the present invention. Such a progression of symptoms may be understood as playing back information that a user submitted over one or more periods in time.

The user may customize certain attributes 1105 to regulate the types of data that will be played back. Such attributes may include which layer(s) will be displayed, which specific symptoms will be used in the visualization 1110, the time range over which to display symptoms 1115, the rate of the playback 1120, etc.

Upon initiation of playback, the system can query the DBR for symptom data, sort the data by date and time, and filter by user criteria (1125). Then, the filtered data may be loaded onto the model in a time dependent fashion. For example, suppose the user indicates the desire to play back symptom data from a given time range at a given rate, say 10 hours of data in 10 seconds. Then, if the system updates the visual representation every second, it may seek to load symptom data inputted over that time duration at 1 hour intervals. For each time point (1130) at which the processor 101 seeks to update the display, filtered data corresponding to that time (1135) will be used to update stores in memory (102, such as a representation of the virtual 3D scene), and update the visual representation (1140). Alternatively, the system may collate symptom data for each hour into a point snapshot for that interval using a variety of techniques such as maximum value, average value, etc. and associate the point snapshot with each second display.

Subsequently updating the visual representation with data from time points at regular intervals may create a flowing experience similar to watching a film. In one specific embodiment, the rate of playback is 0, which allows users to step forward or backward through time manually. Further additional embodiments may include a subset of the following functionalities: rotate or reposition the view during playback, pause playback, play backwards through time, adjust rate of playback during play.

In certain embodiments, it may be desirable to display a visual representation that combines data from one or more times and one or more Body Layers. For example, this feature could be used to observe if symptoms predominantly occur in certain parts of the body. Another instance when this may be desirable would be if one wished to visualize merged data from multiple DBRs representing multiple people. A single visual representation could, for example, be used to see how painted data overlaps on different living beings who were administered the same treatment.

Figure 12:
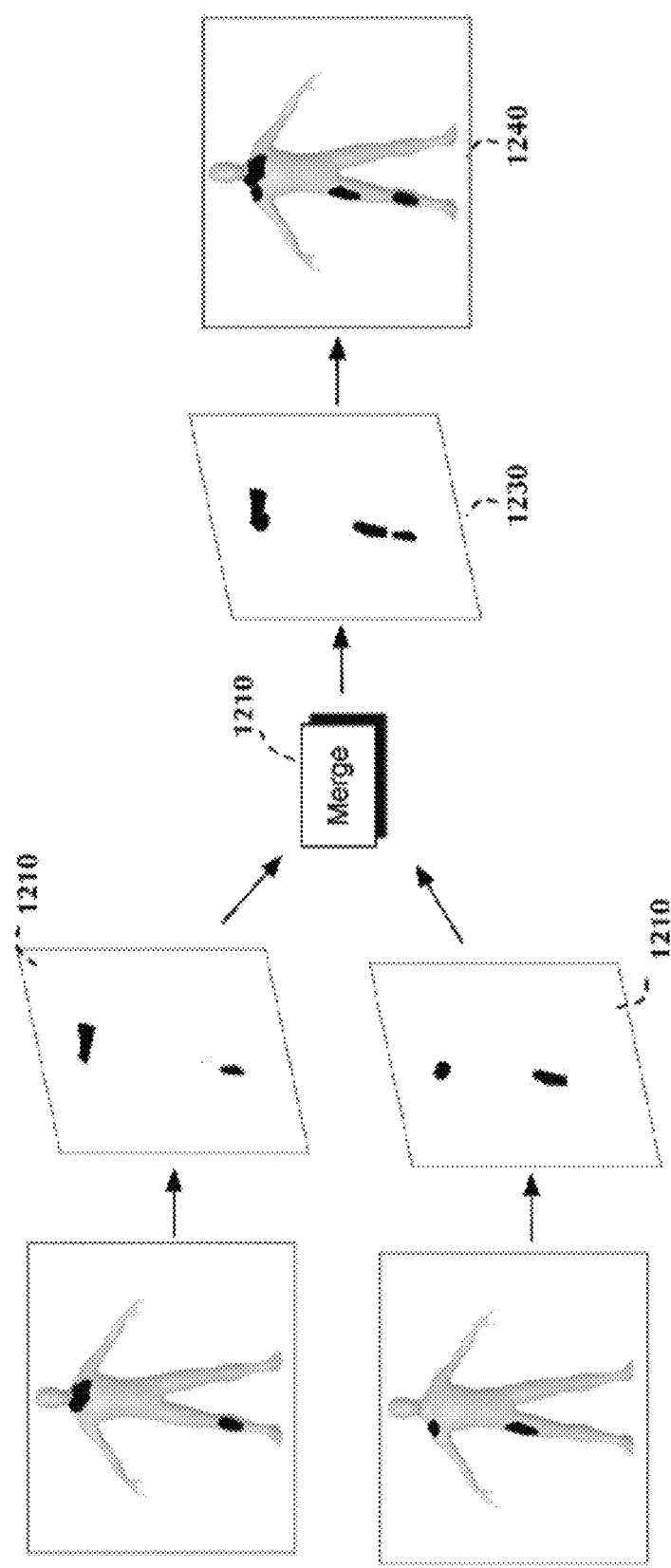
FIG. 12 illustrates an exemplary flow of steps in a method for analyzing user symptom data indicated over a period of time to generate and display a result symptom in a specific embodiment of the present invention.

FIG. 12 illustrates an exemplary flow of steps in a method for analyzing user symptom data indicated over a period of time to generate and display a result symptom in a specific embodiment of the present invention. The user may customize certain attributes (such as via a GUI) to regulate the types of data (such as format of data: textual, visual, painted data, etc.) which will be played back; attributes may include which layer(s) will be displayed, which subset of symptoms will be used in the visualization, the time range over which to merge symptoms, etc. The system may query the DBR for symptom data, sort the data by date and time, and filter by user criteria. In this specific embodiment, the process of merging data objects (e.g. a series of textures, for the painted data format) occurs over a series of steps. These steps involve processing the input symptoms (such as texture objects 1210 1220) to combine the data 1225, and finally appending the calculated data (the result symptom, 930) to the DBR, where it can be used to update the display. At that point data may be used in conjunction with existing routines to modify the visual appearance of the displayed Body Layer(s) 1240.

In a specific embodiment, painted data taken from the same layer over a different times are merged by combining texture pixel data, pixel by pixel, in a repeated fashion. In an additional embodiment, the pixel data are combined in an additive process, where attributes such as intensity are used to create additive representations while merging. Additional techniques may be used to combine symptom data including various image-filtering techniques.

In an alternative embodiment, symptom data (including painted data) from multiple layers may be combined. Thus the result symptom may express data from multiple layers. One method to implement multi-layer merging involves using rays to create a mapping between layer textures, which may be stretched around differently shaped 3D models. For example, a point on the inside of the plurality of layers is chosen and several rays are projected outwards in several directions. Locations where some of these rays intersect multiple layers may be used with corresponding texture mapping data to create a table that maps coordinates between textures of different Body Layers. Then a data combination function, such as an additive calculation, may be used. Once the data are combined, a resulting texture can be displayed showing merged symptom data.

Figure 13:
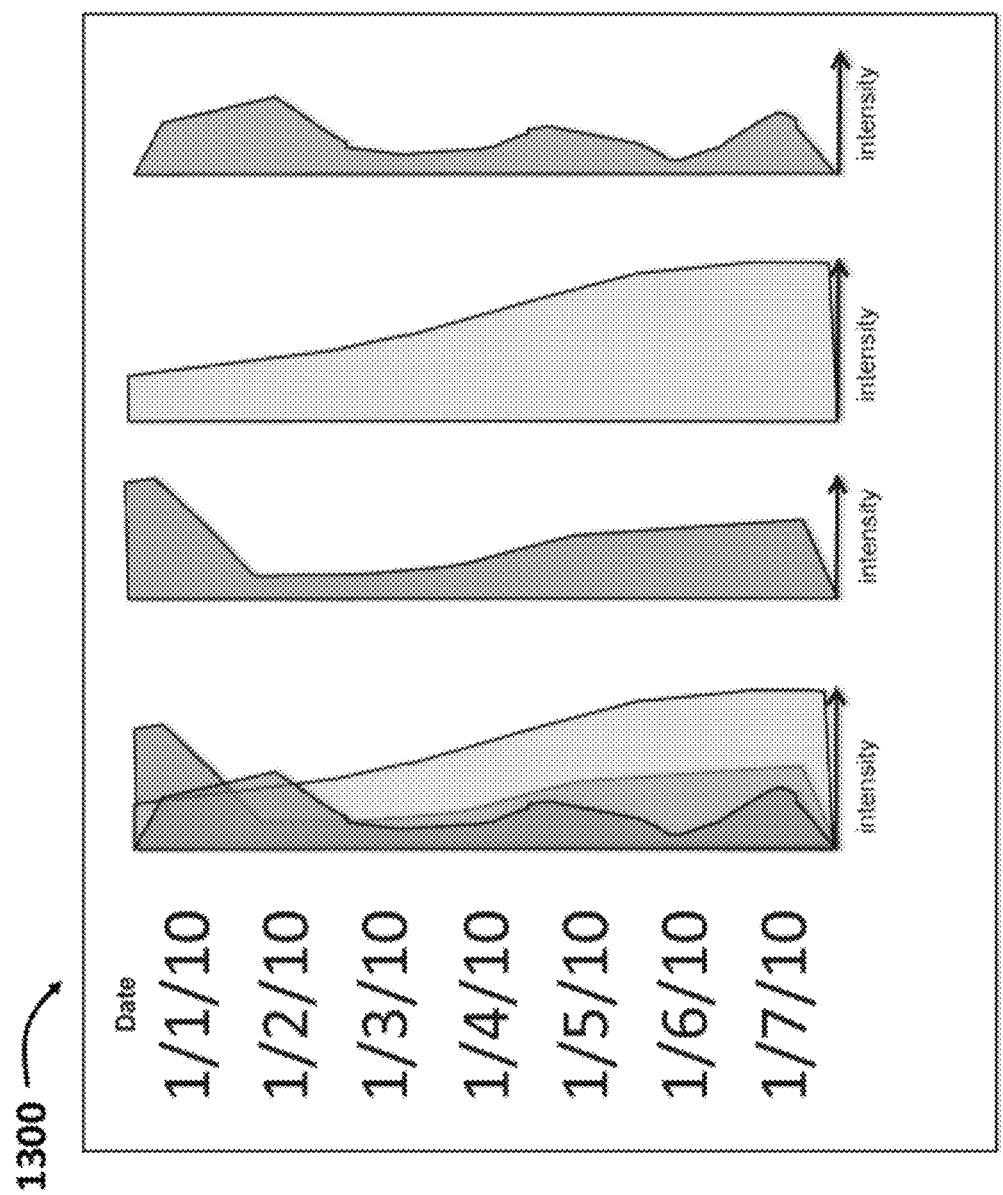
FIG. 13 illustrates an exemplary flow of steps in a method for predicting the cause, treatment, and/or forward-projected symptoms of a living being in a specific embodiment of the present invention.

FIG. 13 illustrates an exemplary computer screenshot for a computer-generated calendar result symptom in a specific embodiment of the present invention. The calendar may also be understood as indication of the change in a symptom (for example, intensity, in this case) over time.

The user may customize some attributes to regulate the types of painted data that will be used to form the calendar result symptom; attributes may include which layer(s) will be displayed, which subset of symptoms will be used in the visualization, the time range over which to display symptoms, etc. The system may query the DBR for symptom data, sort the data by date and time, and filter by user criteria.

In the specific embodiment, the system can access an object which contains model-zone mapping data, which indicates the spatial region corresponding to a physical portion of the body (e.g. arm, leg, or quadrant, etc.), but does not necessarily reflect a grouping represented by the layers. For example, with layers of bone, skin, and muscle, some regions may include upper body and lower body, or left hip, left thigh, left calf, left heel, etc. The model region mapping relates individual polygons in a model to a particular zone. Additionally, since polygons in the model may be associated with texture coordinates, it may be possible to map texture coordinates to regions.

In the specific embodiment, the calendar takes the form of a 2D graph showing intensity versus time for a series of regions. To calculate intensity of a symptom at a given time in a given region, textures from multiple layers may be parsed as described by the following sequence of steps. An embodiment utilizing the sequence of steps below may represent different symptoms as different colors on a texture file (e.g. swelling may be indicated by a distinct color from itching).

In one specific embodiment, every layer may be analyzed at times chosen by the user and inputted into the GUI. For each spatial coordinate in the texture file of the layer, if the corresponding vertex is in the region chosen by the user, the content of the texture file at that point will be analyzed. If the texture file contains data that indicate a symptom at that point (e.g. a colored pixel), the intensity of that symptom will be returned and displayed on the calendar, possibly grouped with the intensity values of other points in the region, as chosen by the user.

In an alternative embodiment, a result symptom is created by summing the intensity of the symptom at a given point on the texture file with the symptom intensity of the corresponding spatial location on every other layer chosen by the user. This summation returns a combined intensity across layers by region.

In an embodiment, a variant of above sequence can be adapted and used to plot points that express intensity of one symptom against time. Additional embodiments may determine intensity of more than one symptom in a zone. In another embodiment, the calendar described may be exported into a commonly understood format (such as XML).

Under certain circumstances, it may be desirable to use data stored within a DBR to model aspects of a person's health. In a specific embodiment of the present invention, over any duration of time, a person's health can be understood as a combination of certain variables (health variables) that may each take on a range of specific values. For example, these variables can be symptoms, treatments, and/or medical condition. In the specific embodiment, data contained within DBR is used to calculate the relationships between these variables and to make predictions answering questions about a person's health.

Figure 14:
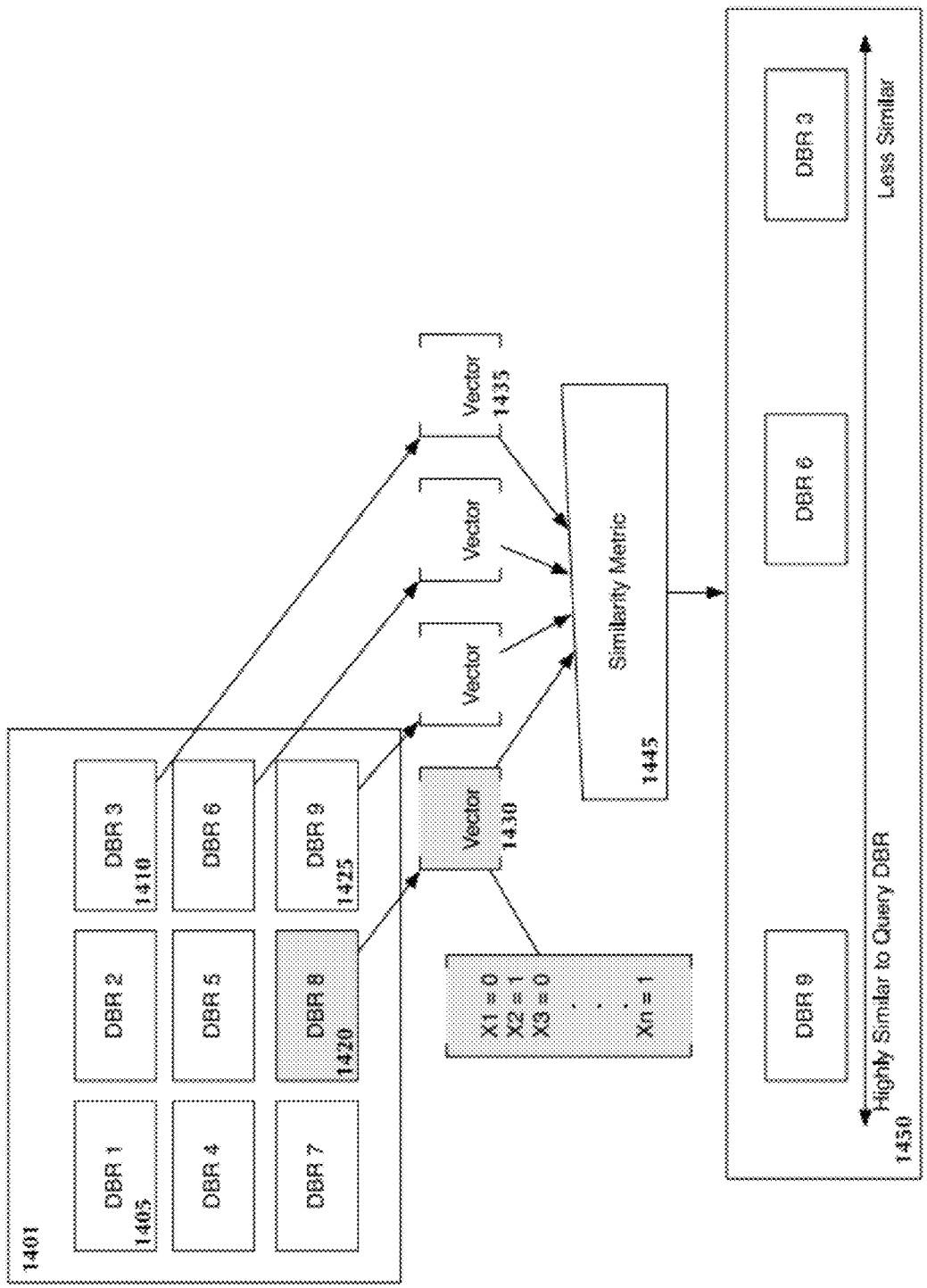
FIG. 14 illustrates an exemplary flow of steps in a method for finding DBRs that are similar to a query DBR in a specific embodiment of the present invention.

FIG. 14 illustrates an exemplary flow of steps in a method for finding DBRs that are similar to a query DBR in a specific embodiment of the present invention. This specific embodiment can advantageously facilitate communication between people with similar medical conditions. This can help in creating a feeling "you are not alone" which can be very soothing for persons in distress. Users can also share their experiences using social network. The users can benefit from advices and experiences of other who face similar medical conditions. This can also help users know about the diagnosis and treatment others with similar medical symptoms received. In an embodiment, the system can send alerts to users to join specific social network when DBR similarity is detected with the specific social network. Communication in a social network can be in the form of short messages, status updates, tweets, emails, discussion forums, blogs and other appropriate techniques.

In this specific embodiment, a plurality of DBRs, representing a plurality of living beings may be stored in computer memory (1401). Then, given a DBR corresponding to a first living being (a query DBR, 1420), it may be desirable to find one or more DBRs corresponding to a second living being, deemed "similar." In a specific embodiment of the present invention, the task of finding similar DBRs can be understood as an unsupervised or partially supervised learning task, where the aim is to use a subset of the data stored inside DBRs to cluster them into similarity groups (clusters). The term unsupervised learning means that objects to be classified are not class labeled, a priori; in clustering, the aim is to group data that may be of the same class.

First, data from a subset of DBRs in the system are reduced into a vector (such as 1430, or 1435) of features, where a feature may be understood as a combination of data objects in a DBR such as a numerical combination, discrete barcodes representing combinations of data, discrete tags representing combinations of data, Boolean data (1440) reflecting processed data, etc. Notice that in general, features may be discrete or continuous in type. Then a similarity metric (1445) may be used to find similar DBRs or rank them by similarity (1450). In one embodiment, similarity is determined by using Hamming distance as an estimator for similarity between any two DBRs, where the Hamming distance between two sequences of equal length is the number of positions at which the corresponding symbols are different. In this specific embodiment, the Hamming distance between DBRs of similar living beings would be hypothesized to be small relative to the Hamming distance between DBRs of dissimilar living beings. Hamming distance can be used to order DBRs by similarity to a query DBR (1450).

In alternative embodiments, Hamming distance, or a similar distance metric may be further employed to apply a technique called Locally Sensitive Hashing, which has been applied to several problem domains including image similarity identification, gene expression similarity identification, and audio similarity identification. In yet alternative embodiment, a nearest-neighbor algorithm can be used to construct an M-dimensional Tree, which is a space-partitioning data structure, for organizing points in an M-dimensional feature space. In a further alternative embodiment, clustering can be implemented by a by kernel estimator. Persons of ordinary skill in the art can contemplate additional clustering techniques for the purpose on comparing DBRs to query DBR and they are included within the scope of the present invention.

In an embodiment, the process for finding similar DBRs may include the construction and querying of a hierarchical data structure, which groups similar DBRs. Such a data structure is a Clustering Decision Tree (CLTree), described in detail by B. Liu, X. Yiyuan, P. Yu in "Clustering via Decision Tree Construction," Published in "Proceedings of the ninth international conference on Information and knowledge management" (2000), herein included by reference.

Depending upon the embodiments, similarity can be understood in terms of a Boolean variable or a non-Boolean variable. Two DBRs can be similar or dissimilar (Boolean), or they can be similar to a degree. Both representations of similarity are consistent with the present invention. A continuous similarity value may be converted to a Boolean via a threshold function (such as a sigmoid or step function). In further additional embodiments, additional schemes and metrics may be used to assess similarity between DBRs, for example, combination of Boolean and non-Boolean variables.

In certain embodiments, information about similarity can be utilized to form a social network, which is a structure made up of individuals called "nodes", which are connected by one or more specific types of interdependency. In this specific embodiment, for each user of the system, there is provided a data-storage object (User object) that represents that user, which may contain attributes referencing DBRs that the user uses. Then, the social network can be formed by establishing connections between User objects that use DBRs, which are found to be similar according to certain predetermined and/or user selectable criteria. For example, a social network can be formed among users with ages 30-40 who experience lower back pain 20% of the time during a day.

In an alternative embodiment, the social network can be formed by repeatedly selecting a first user and querying other users for similarity to the first user, where links may connect the first user to similar users. In an additional further embodiment, the links in the social network may be dynamically updated based on how the similarity between, for instance, two people may change over time. For example, at for some durations of time, two individuals may have very similar symptoms and may benefit from therapeutic aspects of knowing someone else with similar symptoms. However, at some point the similarity between these two people may change, so that they start to become more different; for example, one person's condition could suddenly change and improve. Thus the connections between users may also be updated over time to reflect changes in similarity. This may be implemented by constructing social-networks based on similarities multiple times over a duration.

The User object may contain attributes, which can be used to represent links to other User objects. Determining which users should be linked and how the linkage should take place can be determined by assessing DBR similarity, as previously discussed, then extending the similarity relationships between DBRs to the User objects. For instance, users of DBRs that are deemed similar may have links connecting them.

In an alternative embodiment of the present invention, the nodes of the social network may be DBRs. For example, the links between these nodes may be extended from DBR to DBR. Thus, in an additional embodiment where the social network is used for social purposes, such as for user to user communication, the users are connected to each other based on the medical records that they may access.

In one embodiment of the invention, this extension of DBR similarity to users requires additional logical processing. For instance certain types of links may be suited for certain types of users. For example, some users who are doctors/nurses/therapists that advise a large number of patients may be treated differently than users who are primarily patients.

Under some circumstances, a social network may be used to facilitate the exchange of information between two or more users, where the exchange may depend in some way on the linkage relationships between the users. For instance, in one specific embodiment of the invention, a first set of users who are all directly and mutually linked may communicate with each other via an interactive forum that is exclusive to users in the first set, so that another user, who is not directly linked to a user, in the first set may not participate. Several computer tools and software are readily available today to implement social networking interaction. For example, several open source web application frameworks (including Django and Ruby on Rails) employ a reusable-app feature that simplifies the rapid construction of social web applications. One such package of social applications for Django is an open-source collection of tools called Pinax.

In an alternative embodiment, the social network uses DBRs as the nodes for storing linkage information as opposed to the User object. In a further additional embodiment, a link between nodes is not necessarily Boolean, but is a value which indicates which indicates the strength of the link; such a value may be discrete or continuous. In an additional embodiment, the strength of the link between two users may influence how they may exchange information.

Under certain circumstances, it may be desirable to use data stored within a DBR to model aspects of a person's health. In a specific embodiment of the present invention, over any duration of time, a person's health can be understood as a combination of certain variables (health variables) that may each take on a range of specific values. For example, these variables can be symptoms, treatments and medical condition. In the specific embodiment, data contained within DBR is used to calculate the relationships between these variables and to make predictions answering questions about a person's health. Furthermore, analysis based on these variables may employ the use of similarity relationships between people to make predictions.

Figure 15:
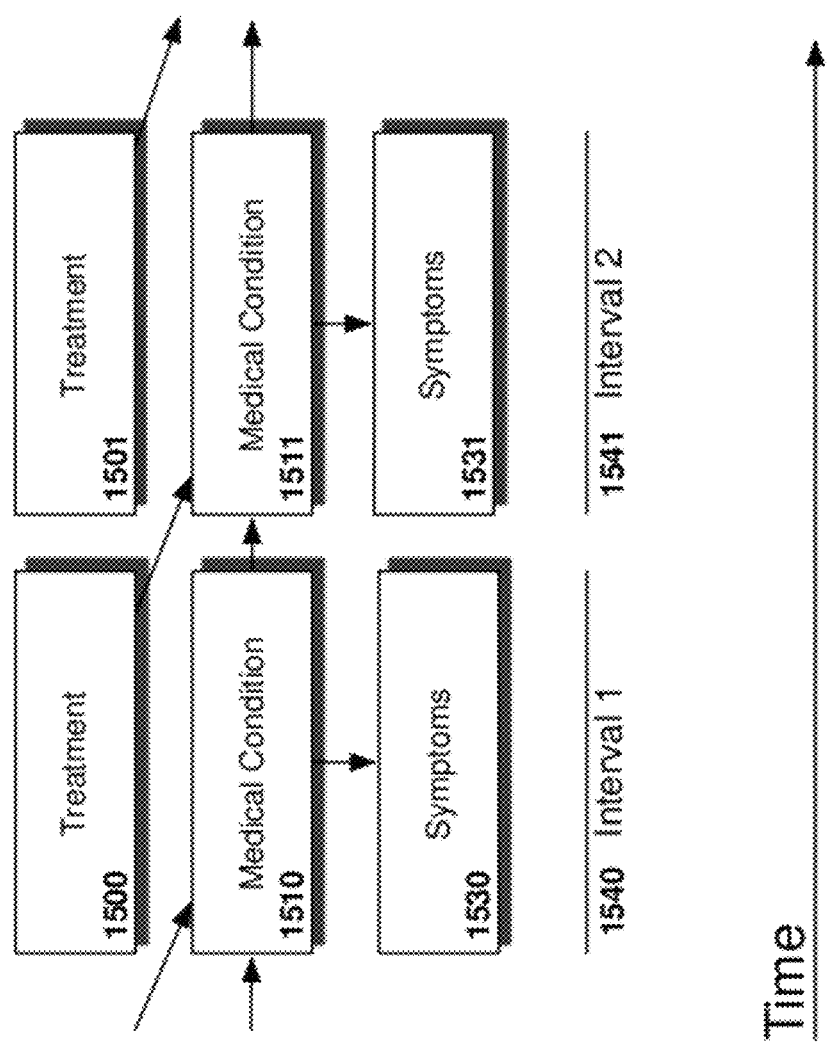
FIG. 15 illustrates temporal relationships between these variables in a specific embodiment of the present invention.

FIG. 15 illustrates temporal relationships between these variables in a specific embodiment of the present invention, where each box represents a specific variable at specific time interval (e.g., from intervals 1531 and 1532). A symptom variable (such as 1520) can be understood to represent a subset of the symptom data from a specific time range (such as 1530). The total range of values that can be assumed by a symptom variable can be understood as the set of various combinations of symptoms that can be stored within a DBR. For example, symptoms may include: pain in upper abdominal muscle, pain in lower abdominal muscle, numbness in skin, restless legs, etc., blurry vision, etc. A medical condition variable (such as 1510) can be understood to be the true physical/biological cause or causes for the person's symptoms (1530) over a particular time interval (such as 1530). The possible range of values for a medical condition variable may include the set of known conditions/diseases/disorders known to affect living beings. For example, a medical condition variable may include values of liver condition, heart condition, thyroid condition, lung condition, etc. A treatment variable (such as 1500) may be understood as one or more actions and behaviors a person may take during a time interval (such as 1520). Some of these treatment actions/behaviors (1500) may include a person's reactions to symptoms from the same time interval (1520). The total range of values that can be assumed by a treatment variable can be understood as including one or more known medical treatments, and/or set of actions a person may take over a period of time. For example, treatments may include vitamin intake, cholesterol pills, stimulants, prescription medication, surgical procedures, exercise regiments, etc.

In the specific embodiment, arrows connecting the boxes represent dependency relationships between health variables; for example, an arrow from a parent-variable, A, to a child-variable, B suggests that the value of the variable B may depend/be influenced by the value of the variable A. The illustration of the specific embodiment shows three types of arrows between various types of variables. An arrow is directed from Medical condition (such as 1510) to symptom (1520) in the same time range. This arrow can be understood by the notion of symptom being due to an underlying cause, which is the medical condition. Another arrow goes from one medical condition variable (such as 1510) to another medical condition variable (1511) at the next time step. This arrow can be understood by recognizing that the medical condition relates to some intrinsic properties of the individual's physiological body that persist through time. A simple example may assist in clarifying what these first two arrows mean. Consider a person who has a painful sore throat (symptom, 1520) one day, which is actually due to a bacterial infection (1510, a medical condition), it may be reasonable to think that some symptoms will persist for several days if the infection. Suppose the next day, the person also has a sore throat, and additionally has fever (1521). The specific embodiment may explain the progression of the symptoms using the medical condition variable 1511: the bacterial infection (1510), which caused the symptoms on the first day (1520) persisted and progressed in the person's body over the course of time, so that on the next day, the body condition was an even more larger infection (1511) causing more pronounced symptoms (1521).

In the present embodiment, the previously mentioned, third arrow, signifies the relationship between a treatment variable (such as 1500) and the subsequent medical condition (1511). This relationship can be understood by recognizing that any action/behavior a person does at a given time may influence the physical/biological state of the body in immediately after the action is competed; thus, it influences the medical condition in a subsequent time interval.

The relationships between the variables illustrated by arrows in FIG. 15 can be understood in stochastic terms. That is, the relationship described by an arrow may actually be observed only a fraction of the time. This is because no matter how specifically a model may try to model the body of a living being, it is not possible to be completely certain about a prediction. Some causes for this uncertainty could be error that comes from the process of recording and storing medical symptom data. Another cause for such error may be the sheer complexity of the body, which makes it hard to model. A specific embodiment of the present invention deals with uncertainty by adopting a probabilistic approach to make predictions about health variables.

Probability can be understood as a framework for working with uncertainty in variables. In the case where a variable's value is known with certainty, that variable can be defined as a particular value; however, in the case where the variable's value is not known with absolute certainty, a probability distribution may be used to express the range of values that a variable is likely to assume. An example of a probability distribution is a normal Gaussian distribution (sometimes called a bell-curve). This distribution describes a variable with an average value and a standard deviation, which describes the spread of the distribution. A large standard deviation suggests that there is low certainty about value of the variable, and that it may frequently take on values in a wide range, whereas a small standard deviation suggests that the variable will typically assume a value close to the mean.

In a specific embodiment of the present invention, health variables can be described by a categorical probability distribution. A categorical probability distribution of a variable, which can assume k-states, can be understood as a collection of k-numbers, where each number is a probability that the variable is a specific state.

During prediction, the specific embodiment determines categorical distributions for variables using a list of states (scenarios) that each variable can assume.

In a specific embodiment, a probability model is constructed reflecting aspects of the relationships between variables described in FIG. 15. A probability model can be understood as a mapping, or as a function, which uses input data to calculate probability distributions (such as a categorical distribution) over the states (scenarios) of unknown, uncertain variables. In an additional embodiment of the present invention, the probability model contains one or more parameters, which are used to define the mapping. The parameters may be numerical, and their values may be determined by a technique called parameter-estimation or training (described below).

Figure 16:
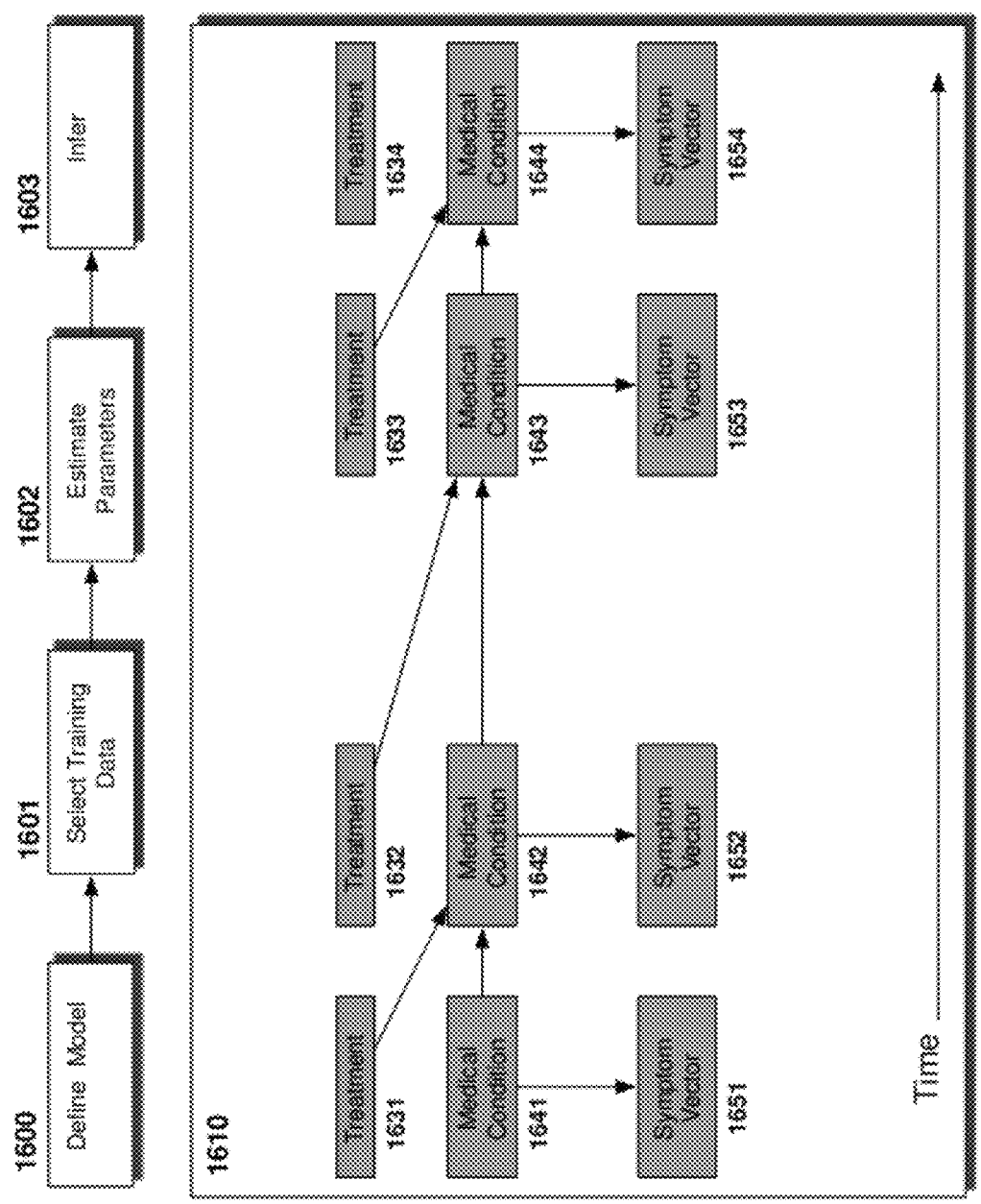
FIG. 16 illustrates an exemplary flow of steps in a method for predicting the cause, treatment, and/or forward-project symptoms of a living being in a specific embodiment of the present invention.

FIG. 16 illustrates an exemplary flow of steps in a method for predicting the cause, treatment, and/or forward-project symptoms of a living being in a specific embodiment of the present invention. The probability model of the specific embodiment can be understood as a Dynamic Bayesian Net, which is a special type of Bayesian network which can be used to model data which have a sequence (such as sequence in time). In the specific embodiment, the process of preparing the Dynamic Bayesian Network can be understood over following steps: defining the network of the model (1600), selecting a set of training data (1601), using said training data to estimate/train the parameters describing the network (1602), and using the parametric data to calculate probability distributions for uncertain health-variables (1603).

In the specific embodiment, defining the Bayesian network (1600) can be understood as the process of indicating the logical (dependence) relationships that may exist between variables. The specific embodiment uses a pre-defined Bayes net structure (1610), a portion of which is graphically represented to illustrate such dependence relationships between variables (shaded boxes) using arrow notation. Recall that an arrow extending from a parent-variable, A, to a child-variable, B suggests that the value of the variable B may depend/be influenced by the value of the variable A. Notice that the Bayesian Network (1610) can contain multiple types of variables, including the Health Variables in a configuration consistent with the logic illustrated in FIG. 15. In the graph 1610, which represents the network immediately after it has been defined (1600), the arrows between variables indicate that the parent variable may influence the child without specifying how it does so. For example, an arrow between a medical conditions 1641 and a symptom 1651 over the same range of time does not specify how the probability distributions of symptoms (1651) depends on the medical condition (1641), but only that such a dependence relationship may exist. Alternatively, predetermined starting values may also be assigned to probability distributions based upon prevalent knowledge about the relationships.

In the specific embodiment, these relationships between variables are specified during the process (1602) of estimating/training the parameters of the network using information including training data (1601). In the specific embodiment, parameter estimation can be understood as converting patterns within the training data into one or more parameters (1620) using a pre-defined algorithm; thus, the set of training data that is used to in parameter estimation has a direct impact on the quality of the model. In one specific embodiment of the present invention, data from a plurality of the DBRs are used to train the model. In an additional embodiment, the plurality of DBRs includes DBRs that are similar to a query DBR. In an alternative embodiment, data from a single DBR is used to train the probability model.

In a specific embodiment of the present invention, a pre-defined algorithm called Expectation-Maximization is used to train the models of the Bayesian Net, and implementation details may be found in the book, Artificial Intelligence a Modern Approach, 3rd ed by Stuart Russell and Peter Norvig, published by Pearson 2010, which is herein incorporated by reference.

In a specific embodiment of the present invention, the Bayes Net can be queried to produce a probability distribution of a health-variable over a set of scenarios for a specific user. Querying involves using a subset of the data stored in his/her DBR as input to the Bayesian net, and using a combination of pre-defined algorithms to make estimations about an uncertain variable, such as a health variable representing medical condition, treatment or symptom. In the specific embodiment, the algorithms that calculate probability distributions of variables in Bayesian networks can be generally understood as doing iterative calculations.

For illustrative purposes, consider a user of a specific embodiment of the invention who is a runner trying the find out the probability that he will recover from a knee injury in time for a major race in the future. Assuming the specific embodiment employs the use of structured Dynamic Bayesian Net (1610), whose parameters have been estimated, answering the runner's question becomes a matter of projecting knowledge about the current medical condition 1641 into the future to predict a future medical condition, such as 1643. As previously discussed in relation to FIG. 15, medical condition at a time depends on the previous medical condition and the prior treatments; thus, the condition at the time of the race 1643 depends on an earlier treatment 1632 and an earlier medical condition 1642, which in turn is unknown (because it is in the future) depends on a previous treatment 1631 and a previous medical condition 1641. Thus, an interactive process which projects probability distributions of the runner's medical condition and treatments into the future one time-step at a time, can calculate a distribution over medical conditions at a time in the future.

Many computational techniques and algorithms may be used to query the Bayesian net and determine probability distributions for different types of variables including medical condition, treatment, and symptoms at different points in time. In one embodiment of the invention, an algorithm known as exact inference may be used to calculate a probability distribution for any node in the network using mathematical probability relationships implicit in the structure of the network. This technique can be applied to calculate distributions for medical condition, treatment, and symptom variables at the current time-interval, future-time intervals and past intervals. In an additional embodiment aspects of the exact inference algorithm are replaced by algorithms called forwards and backwards algorithms, commonly used in statistics and robotics to solve a class of problem called a Hidden Markov Model. In an additional embodiment, a pre-defined sampling scheme may be used to determine probability distributions of uncertain variables in a Bayesian net, where examples of sampling schemes include Gibbs Sampling, and Particle Filtering.

In an alternative embodiment, the relationships between the health variables may be different. In a further additional embodiment, the Bayesian network may include a subset of the health variables described, and may additionally contain additional variables. Alternative embodiments of the present invention may use a probability model different from a Dynamic Bayesian Network, including parametric and non-parametric models to calculate distributions over health variables. In additional embodiments of the present invention, rather than outputting a probability distribution, the model outputs the maximum likelihood, or maximum-a-priori, or Bayesian estimate for a variable. It is to be understood the specific references to statistical models and procedures above is for illustrative purposes only. Persons of ordinary skill in the art can contemplate various alternatives and modifications, which are to be included within the scope of the present invention.

Additional embodiments may include following additional or alternative features: the DBR may be represented in multiple ways; the DBR representation may assume multiple forms in memory at different instances in time (for example, format may change to back up data in a relational database, such as MySQL); the 3D model data may be stored in a coordinate system different than Cartesian; the display information of the surface on a 3D model may be stored by a data object different from a 2D Texture image (e.g. 602); layers may contain a mapping information to portions of a 3D model; the DBR may be implemented in a relational database; 3D Body Layers may be custom made for living beings and/or customized from base template; two or more body layers may include the same 3D structure, but may display different depths of the body using alternative textures, and or texture-mapping; different living beings may have a different collection of layers; any layer may be constructed de novo for each person; any layer may be customized from base template for any living being; the layers may be constructed utilizing body scans, the layers may be modeled in 3D modeling software such as Maya provided by Autodesk of San Rafael, Calif.; more than one texture can be used to add detail to a 3D model's surface; vector-based images (such as SVG format images) are used as texture-files; texture information may be stored in a format different from 2D texture-image; the system and method may be used for animals; audio data can be used in the methods for prediction of health-variables, for example a voice-recognition software can extract words, which can be analyzed and sorted into feature vectors, which can be used for probabilistic modeling.

Alternative embodiments may provide one or more following features: embodiments may use special and/or general purpose hardware and/or software for achieving aspects of interactivity including the display of the Body Layers and the processing of user input; other input devices (e.g., 107) in addition or instead of the pointing device described in illustrative embodiments; other output devices (e.g., 108) may be used in addition or instead of the computer screen described in illustrative embodiments; the steps of layer-selection, symptom selection, and navigation may be performed in different order and combination; the selection of layers, indication of a symptom type, transformation of the layers, and or the input of additional user input may be handled by non-GUI elements, or GUI elements in a different configuration than those described; additional symptom types may be painted besides than those indicated including irritation, itch, tingling, swelling, burning, crawling, rash, and other medical symptoms; additional types of data may be tagged generally including all forms of computer-readable data; painted data may indicate gradation/quantity/intensities of symptoms (e.g., severe burn, intermediate burn, mild burn) visually by means including using different colors or shades; painted data may be saved in an object that is not necessarily a texture after parsing and additional processing to extract information from the texture used for displaying; texture data may be stored in a data object via a process that does not require information from a 2D texture (for example, when the user paints symptoms, the 3D coordinates may be collected and processed into a data-storage object after which the 2D texture may be updated to reflect the data object. Various such modifications, extensions and alternatives will be apparent to persons of ordinary skill in the art and are included within the scope of the present invention.

Accordingly, the present invention provides computer based system and method for recording and analysis of medical conditions. While specific embodiments are described herein, alternative embodiments will be apparent to person of ordinary skill in the art, in which one or more acts described herein can be modified, performed in different order, or omitted; without departing from the spirit of the invention. Moreover, one or more acts can be added to those described herein. Such alternatives and modifications are included within the scope of the present invention.

What is claimed is:

1. A computer system for analysis of medical symptoms on a body of a living being, the system comprising:
   a first portion of computer readable medium which stores digital representation of the body, the digital representation comprising representation of a plurality of tissue layers identified with a plurality of distinct body functions, respectively, and wherein each of the plurality of the tissue layers being a three dimensional representation;
   a processor unit;
   a second portion of computer readable medium which stores instructions executable by the processor unit to perform the steps of:
   displaying at least one tissue layer from the plurality of the tissue layers on a display device;
   receiving a first input indicating a locale on the displayed at least one tissue layer;
   receiving a second input associating a medical symptom description to the indicated locale; and
   including information about the medical symptom description and the associated locale in the digital representation of the body.

2. The system of claim 1 wherein the receiving the second input associating the medical symptom description to the indicated locale comprising receiving input to paint at least a portion within vicinity of the locale.

3. The system of claim 1 wherein the second portion of the computer readable medium stores instructions executable by the processor unit to perform a further step of receiving a third input selecting at least one layer from the plurality of the tissue layers for the displaying.

4. The system of claim 1 wherein the second portion of the computer readable medium stores instructions executable by the processor unit to perform a further step of receiving a fourth input to move at least a portion of the displayed at least one tissue layer to indicate movement of the corresponding portion of the body.

5. The system of claim 1 wherein the second portion of the computer readable medium stores instructions executable by the processor unit to perform a further step of receiving a fifth input to turn at least a portion of the displayed at least one tissue layer to be able to indicate the locale.

6. The system of claim 1 wherein the including the information about the medical symptom description and the associated locale in the digital representation of the body further comprising storing a time information indicative of at least one time instant or at least one time period of the medical symptom in the first portion of the computer readable medium.

7. The system of claim 6 wherein the second portion of the computer readable medium stores instructions executable by the processor unit to perform further steps of:
   processing information associated with a plurality of symptoms indicated with a plurality of times, respectively, to generate a result symptom;
   appending information about the result symptom to the digital representation of the body; and
   displaying the digital representation of the body on a display device with the result symptom indicated on it.

8. The system of claim 7 wherein the plurality of the symptoms being associated with the plurality of the locales, respectively.

9. The system of claim 7 wherein the plurality of the symptoms being associated with the plurality of the tissue layers, respectively.

10. The system of claim 7 wherein the result symptom being generated by merging the plurality of the medical symptoms indicated with the plurality of the times, respectively.

11. The system of claim 7 wherein the result symptom indicating a progression of the plurality of the symptoms in relation to time.

12. The system of claim 1 wherein the second portion of the computer readable medium stores further instructions executable by the processor unit to perform the further steps of:
   accessing a plurality of digital representations of bodies of a plurality of livings beings, wherein the plurality of the digital representations being stored in a plurality of portions of computer readable medium, and wherein each of the plurality of the digital representations including information about at least one medical symptom; and
   identifying at least a subset of the plurality of the digital representations that are similar with respect to at least one medical symptom.

13. The system of claim 12 wherein the second portion of the computer readable medium stores further instructions executable by the processor unit to perform a further step of forming an electronic social network among users associated with the subset of the digital representations that are similar.

14. The system of claim 1 wherein the plurality of the tissue layers comprising a digestion layer, a respiration layer, and a nervous system layer.

15. The system of claim 1 wherein the second portion of the computer readable medium stores further instructions executable by the processor unit to perform the further steps of:
   accessing the digital representation of the body stored in the first portion of the computer readable medium, the digital representation including information about at least one medical symptom; and
   computing a probability distribution over at least one set selected from the group consisting of a set of medical treatments that may be appropriate for the at least one medical symptom, a set of future symptoms expected, and a set of medical conditions that may have resulted into the at least one symptom.

16. A computer system for analysis of medical symptoms on a body of a living being, the system comprising:
   a first portion of computer readable medium which stores digital representation of the body, the digital representation comprising representation of a plurality of tissue layers identified with a plurality of distinct tissue types, respectively, wherein the plurality of the tissue layers comprising an epithelial layer, an endothelial layer, and an innervated tissue layer, and wherein each of the plurality of the tissue layers being a three dimensional representation;
   a processor unit;
   a second portion of computer readable medium which stores instructions executable by the processor unit to perform the steps of:
   displaying at least one tissue layer from the plurality of the tissue layers on a display device;
   receiving a first input indicating a locale on the displayed at least one tissue layer;
   receiving a second input associating a medical symptom description to the indicated locale; and
   including information about the medical symptom description and the associated locale in the digital representation of the body.

17. The system of claim 16 wherein the receiving the first input comprises receiving input from a motion sensor utilized by the User experiencing the medical symptom.

18. A method for analysis of medical symptoms, the method comprising:
   generating a digital representation of the body of a user, the digital representation comprising representation of a plurality of tissue layers, wherein each of the plurality of the tissue layers being a three dimensional representation, and wherein the plurality of the tissue layers comprising a skin layer, a muscle layer, and a bone layer;
   receiving a first input from the user to select one tissue layer from the plurality of the tissue layers for the displaying;
   displaying the selected tissue layer;
   receiving a second input from the user to turn at least a portion of the displayed tissue layer;
   receiving a third input from the user indicating a locale on the displayed tissue layer;
   receiving a fourth input from the user associating a description of a medical symptom to the indicated locale; and
   including the information about the medical symptom description, the associated locale, and the turning of the displayed layer in the digital representation of the body.

19. The system of claim 18 wherein the receiving the second input comprises receiving input from a motion sensor utilized by the user.

20. The system of claim 18 wherein the including the information about the medical symptom description, the associated locale, and the turning of the displayed layer in the digital representation of the body further comprising storing a time information indicative of at least one time instant or at least one time period of the medical symptom in the first portion of the computer readable medium.

* * * * *